(12) United States Patent
Patolsky et al.

(10) Patent No.: US 9,304,118 B2
(45) Date of Patent: **\*Apr. 5, 2016**

(54) FUNCTIONALIZED NANOSTRUCTURES FOR DETECTING NITRO-CONTAINING COMPOUNDS

(71) Applicant: Tracense Systems Ltd., Herzlia (IL)

(72) Inventors: Fernando Patolsky, Rechovot (IL); Yoni Engel, RaAnana (IL); Roey Elnathan, Jerusalem (IL)

(73) Assignee: Tracense Systems Ltd., Herzlia (IL)

( \* ) Notice: Subject to any disclaimer, the term of this patent is extended or adjusted under 35 U.S.C. 154(b) by 0 days.

This patent is subject to a terminal disclaimer.

(21) Appl. No.: 14/735,146

(22) Filed: Jun. 10, 2015

(65) Prior Publication Data

US 2015/0362474 A1    Dec. 17, 2015

Related U.S. Application Data

(63) Continuation of application No. 13/703,056, filed as application No. PCT/IL2011/000443 on Jun. 6, 2011, now Pat. No. 9,063,053.

(30) Foreign Application Priority Data

Jun. 8, 2010   (IL) .......................................... 206241

(51) Int. Cl.
*G01N 27/00* (2006.01)
*G01N 33/22* (2006.01)
(Continued)

(52) U.S. Cl.
CPC .............. *G01N 33/227* (2013.01); *G01N 27/00* (2013.01); *G01N 27/4146* (2013.01); *G01N 33/0057* (2013.01); *Y10T 436/17* (2015.01); *Y10T 436/173076* (2015.01)

(58) Field of Classification Search
CPC . G01N 27/00; G01N 27/414; G01N 27/4141; G01N 27/4145; G01N 27/4146; G01N 33/0037; G01N 33/0057; G01N 33/22; G01N 33/227; Y10T 436/17; Y10T 436/173845; Y10T 436/177962; Y10T 436/178459; Y10T 436/25875
USPC ......... 436/106, 111, 116, 117, 149, 150, 181; 422/68.1, 82.01, 82.02, 83, 88, 90, 98; 977/762; 257/414
See application file for complete search history.

(56) References Cited

U.S. PATENT DOCUMENTS 7,619,290 B2   11/2009  Lieber et al.
7,824,619 B1   11/2010  Aviram
(Continued)

FOREIGN PATENT DOCUMENTS

WO   WO 2009/104180   8/2009
WO   WO 2011/154939   12/2011

OTHER PUBLICATIONS

Communication Pursuant to Article 94(3) EPC Dated Dec. 6, 2013 From the European Patent Office Re. Application No. 11736168.3.
(Continued)

*Primary Examiner* — Maureen Wallenhorst

(57) ABSTRACT

Devices, methods and systems for detecting nitro-containing compounds such as TNT, which utilize semiconductor nanostructures modified by a functional moiety that interacts with the nitro-containing compound, are disclosed. The functional moiety is attached to the nanostructures and is being such that upon contacting a sample that contains the nitro-containing compound, the nanostructure exhibits a detectable change in an electrical property, which is indicative of the presence and/or amount of the nitro-containing compound in the sample. Electronic noses for generating recognition patterns of various nitro-containing compounds, made of a plurality of nanostructures modified by versatile functional moieties are also disclosed. The devices, methods and systems are suitable for detecting nitro-containing compounds in both liquid and gaseous states and for detecting a concentration of a nitro-containing compound such as TNT as low as attomolar concentrations.

26 Claims, 11 Drawing Sheets
(8 of 11 Drawing Sheet(s) Filed in Color)

(51) Int. Cl.
  *G01N 33/00* (2006.01)
  *G01N 27/414* (2006.01)

(56) References Cited

U.S. PATENT DOCUMENTS

| | | | |
|---|---|---|---|
| 9,063,053 B2* | 6/2015 | Patolsky et al. | |
| 2002/0117659 A1 | 8/2002 | Lieber et al. | |
| 2005/0247961 A1 | 11/2005 | Zhou | |
| 2010/0022012 A1 | 1/2010 | Lieber et al. | |
| 2013/0115705 A1 | 5/2013 | Patolsky et al. | |

OTHER PUBLICATIONS

International Preliminary Report on Patentability Dated Aug. 10, 2012 From the International Preliminary Examination Authority Re. Application No. PCT/IL2011/000443.

International Search Report and the Written Opinion Dated Sep. 9, 2011 From the International Searching Authority Re: Application No. PCT/IL2011/000443.

Notice of Reason for Rejection Dated Feb. 6, 2015 From the Japanese Patent Office Re. Application No. 2013-513810 and Its Translation Into English.

Official Action Dated Apr. 4, 2014 From the US Patent and Trademark Office Re. U.S. Appl. No. 13/703,056.

Official Action Dated Sep. 12, 2014 From the US Patent and Trademark Office Re. U.S. Appl. No. 13/703,056.

Singapore Examination Report and Singapore Search Report Dated Jul. 5, 2013 From the Danish Patent and Trademark Office Re. Application No. 201209004-9.

Written Opinion Dated May 11, 2012 From the International Preliminary Examination Authority Re. Application No. PCT/IL2011/000443.

Engel et al. "Supersensitive Detection of Explosives by Silicon Nanowire Arrays", Angewandte Chemie International Edition, XP55006077, 49(38): 6830-6835, Aug. 16, 2010.

Riskin et al. "Imprinting of Molecular Recognition Sites Through Electropolymerization of Functionalized Au Nanoparticles: Development of an Electrochemical TNT Sensor Based on Pi-Donor-Acceptor Interactions", The Journal of the American Chemical Society, JACS, 130(30): 9726-9733, 2008.

Tran et al. "The Gas Sensing Properties of Single-Walled Carbon Nanottibes Deposited on an Amitiosilatie Monolayer", Sensors and Actuators B, 129: 67-71, 2008.

Wang et al. "Copolypeptide-Doped Polyaniline Nanofibers for Electrochemical Detection of Ultratrace Trinitrotoluene", Talanta, 79: 376-382, Available Online Apr. 5, 2009.

Xie et al. "Surface Molecular Self-Assembly Strategy for TNT Imprinting of Polymer Nanowire/Nanotube Arrays", Analytical Chemistry, 78(24): 8339-8346, Dec. 15, 2006.

* cited by examiner

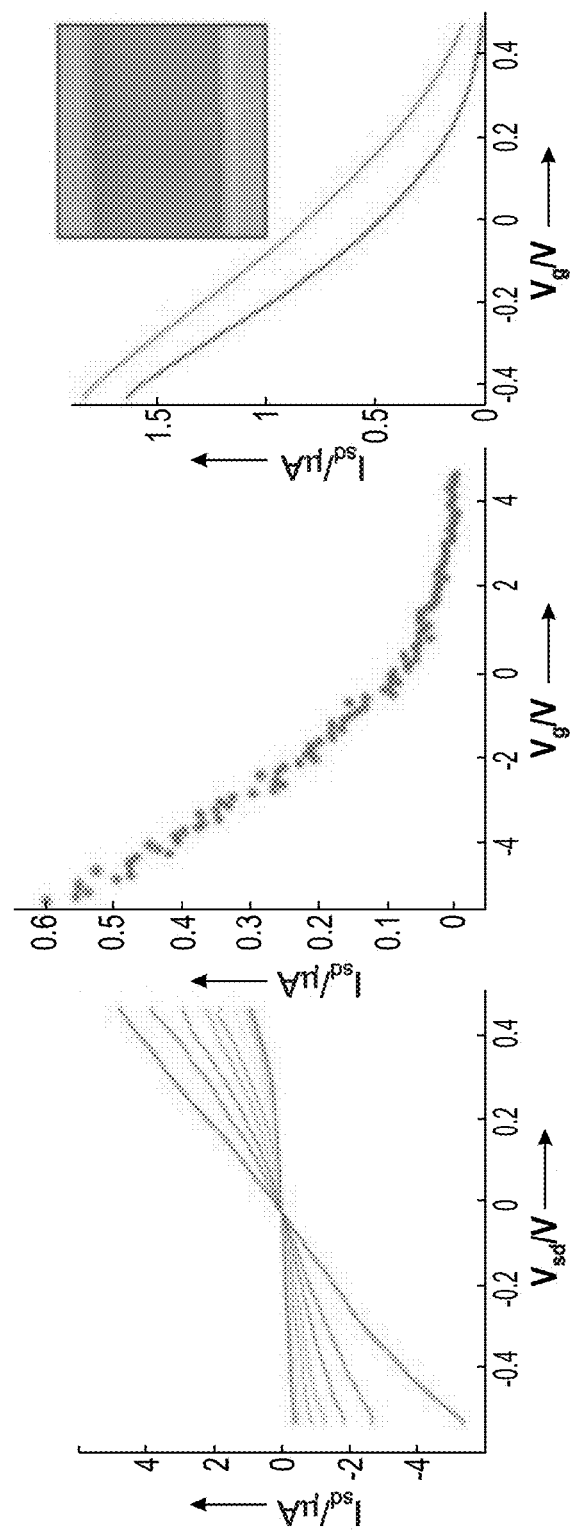

FIG. 11A
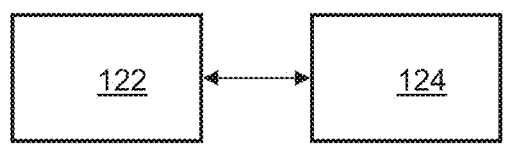
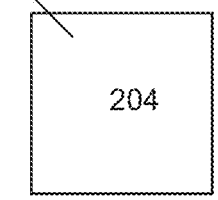
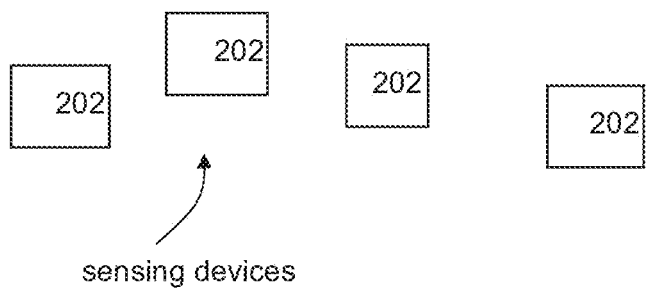
FIG. 11B

FUNCTIONALIZED NANOSTRUCTURES FOR DETECTING NITRO-CONTAINING COMPOUNDS

RELATED APPLICATIONS

This application is a continuation of U.S. patent application Ser. No. 13/703,056 filed on Jan. 21, 2013, now U.S. Pat. No. 9,063,053, issued on Jun. 23, 2015, which is a National Phase of PCT Patent Application No. PCT/IL2011/000443 having International Filing Date of Jun. 6, 2011, which claims the benefit of priority of Israel Patent Application No. 206241, filed on Jun. 8, 2010, now abandoned. The contents of the above applications are all incorporated by reference as if fully set forth herein in their entirety.

FIELD AND BACKGROUND OF THE INVENTION

The present invention, in some embodiments thereof, relates to detection of chemicals and, more particularly, but not exclusively, to devices, systems and methods useful for detecting ultra-trace amounts of nitro-containing chemicals such as explosives in both liquid and gaseous phase.

An 'explosive' is a chemically-unstable molecule having a rapid rate of autodecomposition, with the accompanying evolution of large amounts of heat and gaseous products. There has been a great increase in the development of trace and ultra-trace explosive detection in the last decade, mainly due to the globalization of terrorist acts, and the reclamation of contaminated land previously used for military purposes.

In addition, the availability of raw materials for the preparation of explosives, together with the growing access to information on preparing these explosives, allows for almost anyone with sufficient will and internet access to prepare a bomb. The vast number of people passing through borders, public places, airports etc. poses a huge challenge for current day security screening technologies. The same challenge applies to homes and buildings security. The ultimate goal is of course to be able to rapidly and effectively screen every passing person, without the need to delay the traffic of people, and without human contact if possible.

Explosives, especially concealed ones, have a very low vapor pressure or 'signature' in the surrounding air. The effective vapor pressure of explosives can be reduced by terrorists by a factor of up to 1000, with the use of plastic packages. Detection methods for traces of explosives therefore continue to be plagued by the low volatility of many target analytes.

One of the most commonly-used high explosives over the last 100 years is 2,4,6-trinitrotoluene (TNT), which poses not only a direct security threat, but also great environmental concern due to soil and water contamination near production, storage and test sites.

Analytical procedures in use today for the trace detection of explosives typically involve collecting vapor samples and analyzing them with a sensitive method. Several methodologies have been reported for detecting TNT and other explosives. These are based on electrochemistry, ion-mobility spectrometry, gas chromatography, HPLC, photoluminescence, surface acoustic-wave devices, microcantilevers, fluorescent polymers, surface plasmon resonance, quartz crystal microbalance, immunosensors and other methods. In these existing methods, pre-concentration of air or liquid samples is usually required for a measurable signal to be recorded by the sensor. These procedures are timely, and delay the operation of a sensor. Although some reported methods are very sensitive and selective, most are rather expensive, time-consuming and require bulky equipment, tedious sample preparation and an expert operator. Furthermore, these systems cannot be miniaturized and automated or cannot perform high-throughput analysis.

Table 1 below presents data comparing TNT detection by various currently-employed methodologies.

TABLE 1

| Detection Method | Detection Limit |
| --- | --- |
| remote microelectrode electrochemical sensor in water | 50 ppb |
| luminescent oligo(tetraphenyl)silole nanoparticles in water | 20 ppb |
| quenching of fluorescence of polymer films in air | 10 ppb |
| electrochemical detection by carbon nanotubes in water | 5 ppb |
| biochip (on Au) via QCM or SPR in water | 1-10 ppb |
| electrochemical detection using metallic NP-CNT composites in water | 1 ppb |
| adsorptive stripping by carbon nanotubes-modified GCE in water | 600 ppt |
| electrochemical detection by mesoporous SiO2-modified electrodes in water | 414 ppt |
| oligo(ethylene glycol)-based SPR in water | 80 ppt |
| electrochemical sensing by imprinted electropolymerized bis-aniline-cross-linked AuNPs in water | 46 ppt |
| SPR, fabricated dinitrophenylated-keyhole limpet hemocyanin (DNP-KLH) protein conjugate (in water) | 5 ppt |
| indirect competitive immunoassay using SPR (in water) | 2 ppt |
| SPR sensing by bis-aniline-cross-linked picric acid-imprinted Au-nanoparticles composite in water | $1.2 \times 10^{-3}$ ppt |
| IMS (ion mobility spectroscopy) from air and water samples | 5-10 ppt |
| SAW in water | 10 ppt |
| conducting polymers in water | 20-40 ppt |
| μ-Electron capture detector | 100 ppt |
| Airport sniffers from air samples | 2000 ppt |

Specially-trained dogs can detect explosives with the use of their noses which are very sensitive to scents. These dogs are trained by expert handlers to identify the scents of several common explosive materials and notify the handler when they detect one of these scents. While being very effective, the usefulness of such dogs becomes easily degraded when a dog becomes tired or bored, thus limiting their range of application.

Semiconducting nanowires are known to be extremely sensitive to chemical species adsorbed on their surfaces. For a nanowire device, the binding of a charged analyte to the surface of the nanowire leads to a conductance change, or a change in current flowing through the wires. The 1D (one dimensional) nanoscale morphology and the extremely high surface-to-volume ratio make this conductance change to be much greater for nanowire-based sensors versus planar FETs (field-effect transistors), increasing the sensitivity to a point that single molecule detection is possible.

Nanowire-based field-effect transistors (NW-FETs) have therefore been recognized in the past decade as powerful potential new sensors for the detection of chemical and biological species. See, for example, Patolsky et al., Analytical Chemistry 78, 4260-4269 (2006); Stem et al., IEEE Transactions on Electron Devices 55, 3119-3130 (2008); Cui et al., Science 293, 1289-1292 (2001); Patolsky et al. Proceedings of the National Academy of Sciences of the United States of America 101, 14017-14022 (2004), all being incorporated by reference as if fully set forth herein.

Recently, extensive work has been carried out with the use of nanowire electrical devices for the simultaneous multiplexed detection of multiple biomolecular species of medical diagnostic relevance, such as DNA and proteins [Meng et al., Nature Biotechnology 23, 1294-1301 (2005); Timko et al., Nano Lett. 9, 914-918 (2009); Li et al., Nano Lett. 4, 245-247 (2004)].

Generally, in a NW-FET configuration, the gate potential controls the channel conductance for a given source drain voltage (VSD), and modulation of the gate voltage (VGD) changes the measured source-drain current (ISD). For NW sensors operated as FETs, the sensing mechanism is the field-gating effect of charged molecules on the carrier conduction inside the NW. Compared to devices made of micro-sized materials or bulk materials, the enhanced sensitivity of nanodevices is closely related to the reduced dimensions and larger surface/volume ratio. Since most of the biological analyte molecules have intrinsic charges, binding on the nanowire surface can serve as a molecular gate on the semiconducting SiNW [C M et al., 2001, supra].

U.S. Pat. No. 7,619,290, U.S. patent application having publication No. 2010/0022012, and corresponding applications, teach nanoscale devices composed of, inter alia, functionalized nanowires, which can be used as sensors.

Recently, Clavaguera et al. disclosed a method for sub-ppm detection of nerve agents using chemically functionalized silicon nanoribbon field-effect transistors [Clavaguera et al., Angew. Chem. Int. Ed. 2010, 49, 1-5]. McAlpine et al. [J. Am. Chem. Soc. 2008 Jul. 23; 130(29):9583-9] disclosed a scalable and parallel process for transferring hundreds of pre-aligned silicon nanowires onto plastic to yield highly ordered films for low-power sensor chips. The nanowires exhibit parts-per-billion sensitivity to $NO_2$. $SiO_2$ surface chemistries were used to construct a 'nano-electronic nose' library, which can distinguish acetone and hexane vapors via distributed responses [Nature Materials Vol. 6, 2007, pp. 379-384].

Additional background art includes U.S. patent application having Publication No. 2010/0325073.

SUMMARY OF THE INVENTION

Since considerable attention and ongoing concern has been drawn towards countering terrorist threats and the presence of trace contamination of explosives in soil and groundwater, improved methods are required to facilitate their detection.

The present inventors have now devised and successfully prepared and practiced articles made of modified nanowires, which can be constructed as ultra-sensitive nanosensors that can detect ultra-trace amounts of chemicals selectively, even at gaseous media such as air.

The present inventors have demonstrated the use of such articles as chemical sensors for detecting explosives such as TNT, as well as other nitro-containing compounds.

The present inventors have further showed that "electrical-nose" arrays can be used as an effective platform of unprecedented outstanding detection capability for nitro-containing compounds such as TNT. These arrays can be referred to as "nano-sniffer" arrays.

Thus, a supersensitive, rapid, label-free and real-time detection of TNT and other nitro-containing substances and/or explosives, with the use of large-scale arrays of SiNW-FET devices, chemically-modified with a monolayer of an amine-functionalized silane derivative, e.g., 3-aminopropyltriethoxysilane (APTES), has been demonstrated. This provides a major enhancement of the ability to detect explosive nitro-containing compounds such as TNT.

In some embodiments, strong binding of TNT molecules to the surface of the nanosensors is effected through e.g., an acid-base pairing interaction between TNT molecules and amino ligands on the sensor surface.

The exceptional performance of the SiNW devices enables the detection of TNT with unprecedented sensitivities reaching sub-femto ($10^{-15}$) molar concentrations ($10^{-6}$ ppt).

The nanowire devices described herein can be designed as selective to TNT over other aromatic nitro-containing compounds. Such a high selectivity can be imparted by utilizing a binding mechanism of TNT to the amino-functionalized layer through donor-acceptor, charge-transfer (CT) interactions, as is further detailed hereinunder. The resulting electrostatic attraction provides a stabilizing force for the molecular complex [Xie, C. G. et al. Analytical Chemistry 80, 437-443 (2008); Sharma, S. P. & Lahiri, S. C. Spectrochimica Acta Part a—Molecular and Biomolecular Spectroscopy 70, 144-153 (2008)].

According to an aspect of some embodiments of the present invention there is provided a method of determining a presence and/or an amount of a nitro-containing compound is a sample, the method comprising contacting the sample with a device comprising a semiconductor nanostructure and a functional moiety attached to the nanostructure, the functional moiety being such that upon contacting a sample that contains the nitro-containing compound, the nanostructure exhibits a detectable change in an electrical property, the change being indicative of the presence and/or amount of the nitro-containing compound in the sample.

According to some embodiments of the invention, the sample is a fluid sample.

According to some embodiments of the invention, the sample is air.

According to some embodiments of the invention, the nitro-containing compound is in a fluid state.

According to some embodiments of the invention, the nitro-containing compound is in a gaseous state.

According to some embodiments of the invention, a concentration of the nitro-containing compound in the sample is lower than 1 micromolar.

According to some embodiments of the invention, a concentration of the nitro-containing compound in the sample ranges from 1 micromolar to 1 attomolar.

According to some embodiments of the invention, the functional moiety interacts with the nitro-containing compound by forming a charge transfer complex.

According to some embodiments of the invention, the functional moiety is an electron donating moiety.

According to some embodiments of the invention, a length of the functional moiety is smaller than 2 nm, or smaller than 1.5 nm or smaller than 1 nm.

According to some embodiments of the invention, the functional moiety is selected from the group consisting of $C_{1-10}$ alkyl, $C_{1-10}$ alkenyl, aryl and cycloalkyl, each being substituted by an electron donating group.

According to some embodiments of the invention, the functional moiety is selected from the group consisting of a heteroalicyclic and a heteroaryl, each comprising a heteroatom that functions as an electron donating group.

According to some embodiments of the invention, the electron donating group is selected from the group consisting of amine, alkoxy, thioalkoxy, aryloxy and thioaryloxy.

According to some embodiments of the invention, the electron donating group is amine.

According to some embodiments of the invention, the functional moiety is an aminoalkyl, the alkyl being 1-10 carbon atoms in length.

According to some embodiments of the invention, the alkyl is being 1-5 carbon atoms in length.

According to some embodiments of the invention, the functional moiety is selected from the group consisting aminopropyl and N-methylaminopropyl.

According to some embodiments of the invention, the nitro-containing compound is an explosive.

According to some embodiments of the invention, the nitro-containing compound is selected from the group consisting of 2-nitrotoluene; 3-nitrotoluene; 4-nitrotoluene; 2,4,6-trinitrotoluene (TNT); 2,4-dinitrotoluene; 3,4-dinitrotoluene; 2,6-dinitrotoluene; ethylene glycol dinitrate (EGDN); nitroglycerine (NG); cyclotrimethylenetrinitramine (cyclonite; RDX); pentaerythritol tetranitrate (PETN); homocyclonite (octogen; HMX); ammonium nitrate; 1,2,3-propanetrial trinitrate; and any mixture thereof.

According to some embodiments of the invention, the explosive is TNT.

According to some embodiments of the invention, the nanostructure is a nanowire.

According to some embodiments of the invention, the nanowire has an average diameter in a range of from 0.5 nm to 200 nm.

According to some embodiments of the invention, the nanowire has an average diameter in a range of from 1 nm to 50 nm.

According to some embodiments of the invention, the nanostructure is a nanotube.

According to some embodiments of the invention, the nanotube is selected from the group consisting of a single-walled nanotube and a multi-walled nanotube.

According to some embodiments of the invention, the nanotube has an average inner diameter and/or an average interwall distance in a range of from 0.5 nm to 200 nm.

According to some embodiments of the invention, the semiconductor nanostructure comprises silicon.

According to some embodiments of the invention, the device further comprises a detector constructed and arranged to determine the change in electrical property.

According to some embodiments of the invention, the device comprises or is part of a transistor.

According to some embodiments of the invention, the device further comprises a substrate onto which the nanostructure is deposited.

According to some embodiments of the invention, the device comprises a plurality of the nanostructures being deposited onto the substrate.

According to some embodiments of the invention, the nanostructures are substantially identical.

According to some embodiments of the invention, at least a portion of the plurality of nanostructures comprises nanostructures having attached thereto a first functional moiety and at least another portion of the plurality of nanostructures comprises nanostructures having attached thereto a second functional moiety, the first and second functional moieties are different.

According to some embodiments of the invention, the device is an electronic nanonose.

According to an aspect of some embodiments of the invention there is provided an electronic nanonose comprising a substrate and a plurality of nanostructures deposited onto the substrate, at least a portion of the plurality of nanostructures comprises nanostructures having attached thereto a first functional moiety and at least another portion of the plurality of nanostructures comprises nanostructures having attached thereto a second functional moiety, the first and second functional moieties being different and being such that upon contacting a sample that contains a nitro-containing compound, the plurality of nanostructures exhibits a detectable change in an electrical property, the change being indicative of the presence and/or amount of the nitro-containing compound in the sample, and is further being indicative of the chemical composition of the nitro-containing compound.

According to an aspect of some embodiments of the invention there is provided a system comprising a device as described herein being communicated with a central processing unit, the system being for providing indication of the presence and/or amount of a nitro-containing compound in an environment of the device.

According to an aspect of some embodiments of the present invention there is provided distributed detection system comprising:

a plurality of sensing devices as described herein being deployed over an area and configured for producing detection signals in the presence of a nitro-containing compound; and a central processing unit, communicating with each of the sensing devices and configured for processing the signals and providing indication of presence, amount, location and/or distribution of the nitro-containing compound in the area.

According to some embodiments of the invention, at least one of the sensing devices is deployed statically.

According to some embodiments of the invention, at least one of the sensing devices is mounted on a mobile vector.

According to some embodiments of the invention, the central processing unit is configured for providing indication pertaining to propagation of the nitro-containing compound in the area.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-F present schematic illustrations of the preparation of a nanoarray according to some embodiments of the invention and its use in TNT detection. FIG. 1A presents a schematic representation of APTES surface modification on a silicon nanowire device in a sensor chip according to some embodiments of the invention. FIG. 1B presents a schematic representation of TNT molecules sensing by a sensor chip device according to some embodiments of the invention; TNT molecules are interacting with surface bound APTES amino groups to create strong charge-transfer complexes. FIG. 1C presents a schematic illustration of a set-up for fluid and gas sensing of explosives. FIG. 1D are comparative plots presenting the source-drain current (Ids) versus source-drain voltage (Vds) measured at different gate voltages for an exemplary p-type SiNW FET according to some embodiments of the present invention. The blue, green, black, pink, magenta, yellow, orange, light blue and brown curves (as follow the direction of the arrow) correspond to gate voltage (Vg) values of $-5$, $-4$, $-3$, $-2$, $-1$, 0, 1, 2, and 3 V, respectively. FIG. 1E is a transconductance curve of an exemplary device at Vsd=0.1V. FIG. 1F are plots presenting Ids versus Vg (watergate) recorded for the exemplary p-type SiNW FET device as in FIG. 1D, at a Vds of 1 V, before (red), and after (blue) APTES surface modification. Inset: HRSEM image of an exemplary nanowire device.

FIGS. 2A-D present data obtained in TNT sensing experiments conducted with an exemplary APTES functionalized p-type SiNW FET device according to some embodiments of the invention. FIG. 2A presents the normalized conductance-versus-time of an exemplary APTES functionalized p-type SiNW FET sensor according to some embodiments of the present invention at (Vg=0) recorded following the alternate delivery of TNT solutions of different concentrations ((a) 500 fM, (b) 5 pM, (c) 5 nM, (d) 75 nM, (e) 100 nM, (f) 500 nM, (g) 5 µM) and a reference solution. Inset: Magnification of a single TNT binding/washing sensing event. Blue box denotes the time to reach sensing plateau. FIG. 2B presents the relative percent conductance change ($\Delta G/G_0$) versus TNT concentration (drawn on a logarithmic scale). Inset: a graph demonstrating that the device response is proportional to the concentration of TNT over 3 orders of magnitude. FIG. 2C presents the relative percent conductance change ($\Delta G/G_0$) versus TNT concentration (drawn on a logarithmic scale) for an exceptionally sensitive device according to some embodiments of the present invention. FIG. 2D presents a schematic illustration of the interactions of a TNT molecule with an amino group of the surface bound APTES which create a strong charge-transfer complex that is further stabilized by neighboring amino groups (ammonium functionalities).

FIG. 3 presents response curves of nanowire devices according to some embodiments of the invention to a 5 nM TNT solution modified as follows: (black) APTES-modified nanowire device, (blue) fluorosilane derivative modified device, (red) unmodified (silicon oxide) nanowire device, (green) octadecylsilane modified nanowire device.

FIG. 4 presents the response of an exemplary APTES-functionalized silicon nanowire device according to some embodiments of the present invention towards 5 µM (red) and 5 nM (blue) solutions of 2,4,6-trinitrotoluene (TNT), 2,6-dinitrotoluene, 2,4-dinitrophenol (2,4-DNP), p-Nitrophenol, 1,3,5-Trinitro-1,3,5-triazacyclohexane (RDX) and aniline (top) and the chemical structures of molecular analytes used in the control experiments conducted (bottom).

FIGS. 5A-C present data demonstrating the multiplexed sensing and device stability of a functionalized SiNW FET device according to some embodiments of the present invention. FIG. 5A presents a relative percent conductance change ($\Delta G/G_0$) versus time data recorded simultaneously from three APTES functionalized p-type SiNW FET in an array. The decrease and increase in conductance correspond to times where a 0.1% DMSO/H$_2$O solution spiked with TNT (5 µM) and a reference solution, respectively, were delivered into the fluidic channel. FIG. 5B presents the response of a sensor chip recorded by >30 devices (sequentially), for the sensing of 5 nM TNT. FIG. 5C demonstrates the stability of a sensing device chip according to some embodiments of the present invention for the sensing of TNT, over a period of weeks.

FIG. 6 presents a graph showing gas phase detection of TNT by an exemplary APTES functionalized p-type SiNW FET sensor according to some embodiments of the present invention. Relative percent conductance change ($\Delta G/G_0$) versus time demonstrated after short pulses of TNT vapors in carrier air samples (arrows denote the time when the vapor pulse was performed) show a noticeable decrease in conductance when TNT vapors (at 25° C.) are delivered into the fluidic channel.

FIGS. 7A-B present bar graphs demonstrating sensing of different nitro-containing explosive analytes by differentially-modified nanosensing devices in a single array. Devices colored blue were modified with a stronger electron-donating amine derivative N-methylaminopropyltriethoxy silane. Devices colored in red were modified with APTES. Bars values are an average of the signal obtained by 20 devices modified with APTES and 20 devices modified with N-methylamineTES, respectively. Standard deviation (STD) values are about 10% of reported values.

FIG. 11A is a schematic illustration of a system for determining a presence and/or an amount of a nitro-containing compound according to some embodiments of the present invention.

FIG. 11B is a schematic illustration of a distributed detection system, which can be used for determining a presence and/or an amount of a nitro-containing compound in a region-of-interest according to some embodiments of the present invention.

DESCRIPTION OF SPECIFIC EMBODIMENTS OF THE INVENTION

Figure 1A:
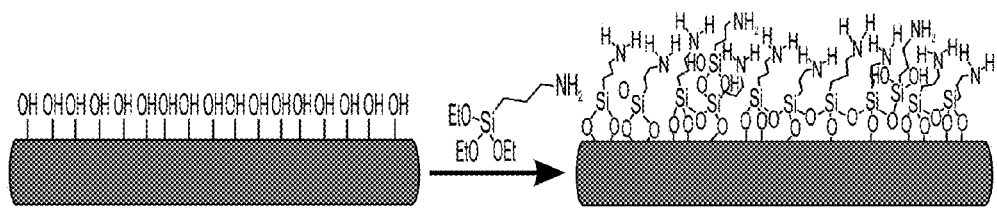
Figure 1B:

The present invention, in some embodiments thereof, relates to detection of chemicals and, more particularly, but not exclusively, to devices, systems and methods utilizing same for detecting ultra-trace amounts of explosives and other nitro-containing chemicals in both liquid and gaseous phase.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

As discussed hereinabove, there is a growing need in the field of detecting chemicals such as explosives for reliable online and real-time monitoring of large areas. To this end, there is a need to develop sensors that are cheap, small, and simple, with ultra high sensitivities and with low power consumption to allow for continuous operation.

The present inventors have recognized that a successful chemical sensor for TNT, and other nitro-containing chemicals and explosives, should exhibit the following features: (1) be extremely sensitive given that the vapor pressure of TNT at 25° C. is as low as $5.8 \times 10^{-6}$ Torr (<10 ppb) [Senesac, L. & Thundat, T. G. Materials Today 11, 28-36 (2008)], and that the vapor pressure of other commonly used explosives, such as RDX and HMX, is even lower, being in the ppt and ppq levels, respectively, (2) be highly selective, eliminating both false positives and false negatives; (3) be robust and not prone to drift; (4) have the ability to be easily miniaturized for, for example, field or home security applications; and (5) be able to perform real-time high-throughput analysis based on arrays of multiple sensing elements.

The present inventors have devised and successfully prepared and practiced articles made of modified nanowires, which can be constructed as ultra-sensitive nanosensors that can detect ultra-trace amounts of chemicals selectively, even at gaseous media such as air.

The present inventors have demonstrated a rapid, label-free, real-time supersensitive detection with high selectivity for TNT and other nitro-containing compounds, with the use of large arrays of chemically-modified SiNW-FETs with a detection limit reaching the sub-femtomolar concentration range. The present inventors have showed that the developed sensors could distinguish TNT from other related compounds, with or without nitro groups, and exhibit a clear concentration-dependent conductance response for TNT.

The present inventors have generated selective and supersensitive electronic noses intended for the detection of TNT and other explosive-chemical analytes, which form a basis towards label-free simultaneous detection of a larger spectrum of explosives and other nitro-containing chemical agents.

These nanosensors can be discreetly stationed, for example, on every street corner, through public buildings, or through a homeland, sampling the surrounding air with the highest sensitivity, all connected to an analysis center.

In one embodiment of the methodology described herein, electron-rich aminosilane monolayer-functionalized SiNW devices are utilized for the label-free, multiplexed real-time and rapid supersensitive electrical detection of TNT, down to a detection limit of about 0.1 femtomolar (about $1 \times 10^{-6}$ ppt). Without being bound by any particular theory, it is believed that the electron-rich amine monolayer on the surface of the SiNW device binds the electron-deficient explosive molecules (e.g., TNT) through charge-transfer donor-acceptor interactions, resulting in charged TNT-amine complexes in close proximity to the nanowire surface, and thus causing sharp changes in the conductance of the electrical-sensing nanoelements. This, in turn, results in an unprecedented detection sensitivity limit for TNT in aqueous solutions, as well as for TNT vapors sampled directly from the air. The supersensitive, simultaneous detection performed by tens, or hundreds, of nanosensors in real-time, has significant advantages over current detection strategies, and allows for more reliable, sensitive and rapid performance, with considerably reduced number of failures. By virtue of the extraordinary sensitivity shown, the sensor platform described herein is not limited by the intrinsic low volatility of most explosive species.

According to an aspect of embodiments of the present invention there is provided a method of determining a presence and/or an amount of a nitro-containing compound is a sample, the method comprising contacting the sample with a device which comprises a semiconductor nanostructure and a functional moiety attached to the nanostructure, the functional moiety being such that upon contacting a sample the contains the nitro-containing compound, the nanostructure exhibits a detectable change in an electrical property, which change is being indicative of the presence and/or amount of the nitro-containing compound in the sample.

The Sample:

As used herein, the phrase "nitro-containing compound" encompasses compounds which include one or more nitro groups, attached to, for example, saturated or unsaturated, linear or cyclic, hydrocarbon backbone.

A nitro-containing compound can therefore be comprised of an aliphatic or alicyclic or aromatic hydrocarbon moiety, substituted by one or more nitro groups. The hydrocarbon moiety can optionally be interrupted by one or more heteroatoms such as nitrogen, oxygen, sulfur, phosphor, silicon, boron.

In some embodiments, the nitro-containing compound comprises an aromatic moiety (e.g., an aryl) substituted by one or more nitro groups.

In some embodiments, the nitro-containing compound is an explosive.

As used herein, the term "explosive" encompasses an explosive material, an explosive residue (e.g., a substance obtained upon explosion) and a material associated with an explosive material (e.g., a starting material for preparing an explosive material).

Exemplary nitro-containing compounds which can be detected by utilizing the methods, devices and systems described herein include, but are not limited to, 2-nitrotoluene; 3-nitrotoluene; 4-nitrotoluene; 2,4,6-trinitrotoluene (TNT); 2,4-dinitrotoluene; 3,4-dinitrotoluene; 2,6-dinitrotoluene; ethylene glycol dinitrate (EGDN); nitroglycerine (NG); nitrocellulose; ammonium nitrate, cyclotrimethylenetrinitramine (cyclonite; RDX); pentaerythritol tetranitrate (PETN); homocyclonite (octogen; HMX); 2,4,6-Trinitrophenylmethylnitramine (Tetryl); picric acid; 1,2,3-propanetrial trinitrate and any mixture and/or formulation thereof, including, for example, 1,2,3-propanetrial trinitrate Formulations (e.g., NitroBid); C-2 (RDX, TNT, DNT and NG); C-3 (RDX, TNT, DNT, Tetryl and NG); C-4 (RDX and PETN), Semtex (RDX and PETN); Detasheet (RDX and PETN); Dynamites (EDGN and NG); Pentolite (PETN+TNT); PTX-1 (RDX, TNT and Tetryl); PTX-2 (RDX, TNT and PETN); and Tetryol (TNT and Tetryl). Some exemplary nitro-containing compounds are presented in FIG. 4.

In some embodiments, the explosive is TNT.

Herein, a nitro-containing compound is also referred to interchangeably as an analyte.

The sample encompasses samples suspected as containing a nitro-containing compound, such that the method described herein is utilized for determining a presence and optionally an amount of a nitro-containing compound and further optionally an identity (e.g., a chemical composition) of a nitro-containing compound. Optionally, the sample is known to contain a nitro-containing compound and the method described herein is utilized for determining an amount and/or identity of the nitro-containing compound.

In some embodiments, the sample is a fluid sample, and can be a liquid sample or a gaseous sample.

In some embodiments, the sample is air.

In some embodiments, the nitro-containing compound is in a fluid state (e.g., is in a liquid state or a gaseous state).

The term "fluid" is defined as a substance that tends to flow and to conform to the outline of its container. Typical fluids include liquids and gasses, but may also include free flowing solid particles.

In some embodiments, the nitro-containing compound is in a gaseous state.

By "gaseous state" it is meant that at least a portion of the compound is in a form of vapors. Thus, for example, the compound can be a liquid or a solid at room temperature, yet, it is volatile to some extent, such that a portion thereof is in a gaseous state at room temperature. Alternatively, the compound can be in such a gaseous state upon heating a sample containing same.

Since, as noted herein, the method described herein can be utilized for detecting ultra-trace amounts of nitro-containing compounds, the portion of a compound in a gaseous state can be ultra-law, as is further detailed hereinbelow.

In some embodiments, a concentration of the nitro-containing compound in the sample is lower than 1 micromolar, lower than 1 nanomolar, lower than 1 picomolar, lower than 1 femtomolar and even is at the attomolar range.

In some embodiments, a concentration of the nitro-containing compound in the sample ranges from 1 micromolar to 1 attomolar, or from 1 microliter to 1 nanomolar, or from 1 microliter to 1 picomolar, or from 1 micromolar to 1 femtomolar, or from 1 nanomolar to 1 picomolar, or from 1 nanomolar to 1 femtomolar, or from 1 nanomolar to 1 attomolar, or from 1 picomolar to 1 femtomolar, or from 1 picomolar to 1 attomolar, or from 1 femtomolar to attomolar.

The concentration of the nitro-containing compound encompasses a concentration of the compound's vapors in air or other gaseous samples, as well as a concentration of the compound in a liquid sample.

Accordingly, in some embodiments, the method described herein can be utilized to detect low-volatile nitro-containing compounds, with ultra-low vapor pressure, without concentrating the sample and/or heating the sample prior to contacting it with the device.

The Device:

As used herein, a "nanostructure" describes an elongated nanoscale semiconductor which, at any point along its length, has at least one cross-sectional dimension and, in some embodiments, two orthogonal cross-sectional dimensions less than 1 micron, or less then 500 nanometers, or less than 200 nanometers, or less than 150 nanometers, or less than 100 nanometers, or even less than 70, less than 50 nanometers, less than 20 nanometers, less than 10 nanometers, or less than 5 nanometers. In some embodiments, the cross-sectional dimension can be less than 2 nanometers or 1 nanometer.

In some embodiments, the nanostructure has at least one cross-sectional dimension ranging from 0.5 nanometers to 200 nanometers, or from 1 nm to 100 nm, or from 1 nm to 50 nm.

The length of a nanostructure expresses its elongation extent generally perpendicularly to its cross-section. According to some embodiments of the present invention the length of the nanostructure ranges from 10 nm to 50 microns.

The cross-section of the elongated semiconductor may have any arbitrary shape, including, but not limited to, circular, square, rectangular, elliptical and tubular. Regular and irregular shapes are included.

In various exemplary embodiments of the invention the nanostructure is a non-hollow structure, referred to herein as "nanowire".

A "wire" refers to any material having a conductivity, namely having an ability to pass charge through itself.

In some embodiments, a nanowire has an average diameter that ranges from 0.5 nanometers to 200 nanometers, or from 1 nm to 100 nm, or from 1 nm to 50 nm.

In some embodiments of the present invention, the nanostructure is shaped as hollow tubes, preferably entirely hollow along their longitudinal axis, referred to herein as "nanotube" or as "nanotubular structure".

The nanotubes can be single-walled nanotubes, multi-walled nanotubes or a combination thereof.

In some embodiments, an average inner diameter of a nanotube ranges from 0.5 nanometers to 200 nanometers, or from 1 nm to 100 nm, or from 1 nm to 50 nm.

In case of multi-walled nanotubes, in some embodiments, an interwall distance can range from 0.5 nanometers to 200 nanometers, or from 1 nm to 100 nm, or from 1 nm to 50 nm.

Exemplary nanotubes and methods of preparing same are disclosed in WO 2010/052704, which is incorporated by reference as if fully set forth herein.

Selection of suitable semiconductor materials for forming a nanostructure as described herein will be apparent and readily reproducible by those of ordinary skill in the art, in view of the guidelines provided herein for beneficially practicing embodiments of the invention.

In some embodiments, the nanostructure is a silicon nanowire (SiNW). Nanowires made of other elemental semiconductor materials, mad semiconductor nanostructures doped with n-dopant or p-dopant, are also contemplated.

In some embodiments, the nanostructure is a silicon nanotube (SiNT). Nanotubes made of other elemental semiconductor materials, optionally doped with n-dopant or p-dopant, are also contemplated.

In some embodiments, the device comprises a plurality of nanowires and/or nanotubes, grown on a substrate by using, for example, chemical vapor deposition. Optionally, once the nanowires and/or nanotubes are obtained, the substrate is etched and the nanowires and/or nanotubes are arranged within the device as desired. Alternatively, nanowires can be made using laser assisted catalytic growth (LCG).

In some embodiments, the device comprises a plurality of nanostructures, e.g., from 2 to 2000 nanostructures per 1 square centimeter. The nanostructures can comprise nanowires, as described herein, nanotubes, as described herein, and combination thereof.

In some embodiments, the device further comprises a detector constructed and arranged to determine the change in electrical property.

Any detector capable of determining a change in the electrical property of the nanostructure can be used.

An electrical property of the nanostructure can be, for example, its conductivity, resistivity, etc., and the detector can be constructed for measuring a change in an electronic property, for example, for measuring a change in voltage, current, conductivity, resistance, impedance, inductance, charge, etc.

The detector typically includes a power source and a voltmeter or amperemeter. In one embodiment, a conductance less than 1 nS can be detected. In some embodiments, a conductance in the range of thousands of nS can be detected.

Figure 8:
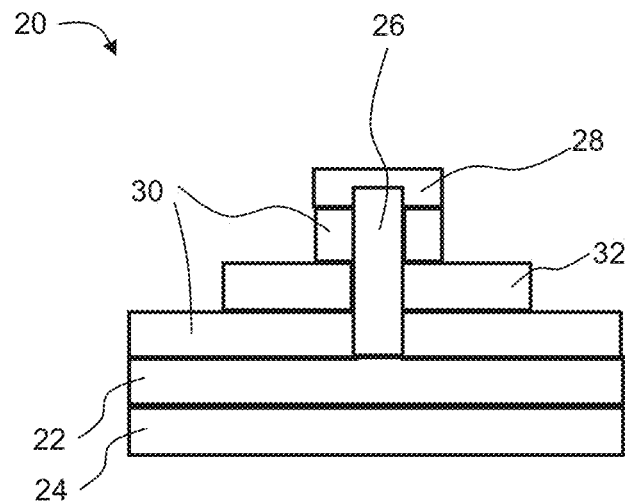
FIG. 8 is a schematic cross-sectional illustration of a transistor according to an embodiment of the present invention.

In some embodiments, the device is arranged as a transistor, such as, but not limited to, a field-effect transistor (FET). An exemplary illustration of this embodiment is illustrated in FIG. 8, which is a schematic cross-sectional illustration of a transistor 20 according to an embodiment of the present invention. Transistor 20 comprises a first electrode 22 acting as a drain formed on a substrate 24, one or more nanostructures 26 acting as a channel and a second electrode 28 acting as a source contacting (e.g., formed on) nanostructure(s) 26. In the non-limiting illustration shown in FIG. 8, nanostructures 26 are aligned vertically with respect to first electrode 22. However, this need not necessarily be the case, since, for some applications, it may not be necessary for the nanostructures to be alighted vertically.

One portion of nanostructures 26 is enclosed by a gate 32, while the remaining portion is shielded by buried layers 30 acting as spacers made of an insulating material to protect and support nanostructures 26. Due to the structure in which gate 32 completely encloses the channel (nanostructures 26), the effect of an electric field around the channel is maximized and a fully depleted depletion layer is obtained by an electric field produced by gate 32.

Figure 9:
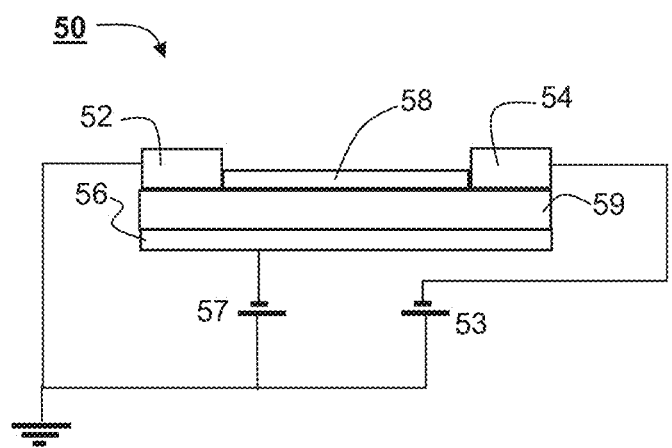
FIG. 9 is a schematic illustration of a transistor, in an embodiment of the invention in which the nanostructures can be aligned generally parallel to the substrate.

FIG. 9 is a schematic illustration of a transistor 50, in an embodiment in which the nanostructures can be aligned generally parallel to the substrate. Transistor 50 comprises a source electrode 52, a drain electrode 54, a gate electrode 56 and a channel 58. One or both of gate electrode 56 and channel 58 may be formed of the nanostructure device of the present embodiments or a plurality of nanostructure devices. For example, in one embodiment channel 58 is a nanostructure or a plurality of nanostructures and gate electrode 56 is, for example, a layer of $SiO_2$ in a silicon wafer. Channel 58 can have semiconducting properties (either n-type or p-type semiconducting properties) such that the density of charge carriers can be varied. Channel 58 can contact the substrate, or in the shown alternative, may be spaced a distance away from the substrate, with or without a layer 59 of intervening material. A gate voltage 57 is applied to channel 58 through gate electrode 56. When the voltage of gate electrode 56 is zero, channel 58 does not contain any free charge carriers and is essentially an insulator. As voltage 57 is increased, the electric field caused thereby attracts electrons (or more generally, charge carriers) from source electrode 52 and drain electrode 54, and channel 58 becomes conducting.

It is appreciated that when the electrical property of the nanostructure varies in response to interaction with a sample that contains the nitro-containing compound, a detectable signal is produced by transistors 20 or 50. For example, a change in the electrical property the source-drain induces a change in the characteristic response of the transistor to the gate voltage (e.g., the source-drain current as a function of the gate voltage), which change can be detected and analyzed.

The device described herein is also referred to as a sensing device or simply as a sensor.

The Functional Moiety:

As noted herein, determining the presence and/or amount of a nitro-containing compound is effected by measuring a change in the electrical property of a modified nanostructure, whereby this change occurs as a result of an interaction between a functional moiety that is attached to the nanostructure and the analyte.

Without being bound by any particular theory, it is assumed that the high sensitivity of the devices utilized in the method described herein stems from the mechanism of action involved in the interaction of the modified nanostructure with the nitro-containing compound, as is discussed in detailed hereinunder.

In some embodiments, the functional moiety interacts with the nitro-containing compound by forming a charge transfer complex.

As defined in IUPAC, a "charge-transfer complex" is an electron-donor-electron-acceptor complex, characterized by electronic transition(s) to an excited state in which there is a partial transfer of electronic charge from the donor to the acceptor moiety.

Since the nitro group in nitro-containing compounds acts as an electron-withdrawing group, nitro-containing compounds typically comprise domains which exhibit a partial positive charge, due to electron resonance between these domains and the nitro group(s).

In some embodiments, the nanostructures composing the device are modified so as to have a functional moiety which is an electron donating moiety, attached thereto.

Without being bound by any particular theory, it is assumed that the electron donating moiety forms a charge transfer complex with the positively charged domains in the nitro-containing compounds.

Thus, in some embodiments, in a charge-transfer complex as described herein, the electron donor in an electron-donating moiety attached to the nanostructure by means of a modified nanostructure, as described herein, and the electron-acceptor is the nitro-containing moiety.

As used herein, the phrase "electron donating" with respect to a moiety or group describes a moiety or group that comprises at least one electron donating atom, as this phrase is defined herein.

As used herein, the phrase "electron donating atom" describes any atom in a chemical group which is capable of donating one or more electrons to an electron acceptor (e.g., an atom or a molecule that exhibits electron deficiency), so as to interact with the acceptor (e.g., via formation of a charge transfer complex). Typically, the electron donating atom is characterized by the presence of a free electron pair. Various heteroatoms (e.g., phosphorus, sulfur, nitrogen) are known in the art to be capable of acting as electron donating atoms. In addition, a carbon atom in an N-heterocyclic carbene (e.g., an N-heterocyclic carbene which is a five- or six-membered heteroalicyclic or heteroaromatic ring described herein) may be a suitable electron donating atom.

In some embodiments, a length of the functional moiety is smaller than 2 nm, smaller than 1.5 nm, and even smaller than 1 nm. This allows the formation of the charge transfer complex to occur close to the nanostructures' surface, thereby enhancing the device's sensitivity.

A detailed discussion of a proposed mechanism of action, described in the context of an exemplary functional moiety and an exemplary nitro-containing compound is presented in the Examples section that follows. This proposed mechanism applies to any functional moiety that features a suitable length and a suitable electron-donating group, and to any nitro-containing compound that is not of a biological nature (e.g., a small molecule).

As used herein and in the art, the phrase "Debye length" describes the distance over which significant charge separation can occur.

In some embodiments, the functional moiety in the device as described herein is elected such that a Debye length of at least 100 nm, at least 500 nm, at least 800 nm and even 1 micron and higher is exhibited.

Without being bound by any particular theory, the advantageous Debye length value stems from the reduced shielding of the charge transfer, which in turn stems from formation of a charge-transfer complex in close proximity to the nanostructure, and from the capability to perform the sensing in solutions with low ionic strength (e.g., deionized water).

Exemplary functional moieties include, but are not limited to, alkyl, alkenyl, alkynyl, aryl and cycloalkyl, each being substituted by one or more electron donating group(s), and each being smaller than 2 nm in length, smaller than 1.5 nm, and even smaller than 1 nm.

In some embodiments, the functional moiety is an alkyl, alkenyl or alkynyl, being from 1 to 10 carbon atoms in length, and being substituted by one or more electron donating moieties.

In some embodiments, the alkyl, alkenyl or alkynyl described herein is being of from 1 to 9 carbon atoms, or from 1 to 8 carbon atoms, or from 1 to 7 carbon atoms, or from 1 to 6 carbon atoms, or from 1 to 5 carbon atoms, or from 1 to 4 carbon atoms, or from 1 to 3 carbon atoms, or from 1 to 2 carbon atoms in length, or of 1 carbon atom in length.

In some embodiments, alkyl, alkenyl or alkynyl described herein is being from 1 to 4 carbon atoms in length.

In some embodiments, the functional moiety is an alkyl being from 1 to 4 carbon atoms in length and comprising one or more electron-donating moieties.

The electron-donating moieties are preferably located at the distal terminus of the alkyl, alkenyl or alkynyl, with respect to the nanostructure's surface, so as to be exposed to interacting with the nitro-containing compound.

In some embodiments, the functional moiety is a cyclic moiety, such as aryl or cycloalkyl, being smaller than 2 mm in length and hence being formed of from 1 to 3 fused rings, and comprising one or more electron-donating group as substituent(s). The substituent is preferably located so as to be exposed to interacting with the nitro-containing compound.

In some embodiments, the functional moiety is selected from the group consisting of a heteroalicyclic and a heteroaryl, each comprising a heteroatom that functions as an electron donating group.

In some embodiments, the heteroatom is nitrogen, being substituted or unsubstituted. In cases where the nitrogen atom is substituted, the substituent is preferably such that enhances its electron donating properties, namely, is a substituent which features an electron inductive effect (e.g., alkyls), yet do not impart steric hindrance (e.g., lower alkyl such as methyl or ethyl).

Exemplary electron donating groups include, but are not limited to, amine, alkoxy, thioalkoxy, aryloxy and thioaryloxy.

In some embodiments, the electron donating group is amine, as defined herein.

The amine can be unsubstituted or substituted, namely, be a primary amine or a secondary amine, as defined herein. In cases where the amine is substituted, the substituent(s) are preferably such that enhance its electron donating properties, namely, are substituents which feature an electron inductive effect (e.g., alkyls), yet do not impart steric hindrance (e.g., lower alkyl such as methyl or ethyl).

In some embodiments, the functional moiety is an aminoalkyl, the alkyl being 1-10 carbon atoms in length.

In some embodiments, the alkyl is being 1-5 carbon atoms in length.

In some embodiments, the functional moiety is aminopropyl.

In some embodiments, the functional moiety is N-methylaminopropyl.

Other suitable functional moieties include, but are not limited to, aminoaryl (an aryl substituted by an amine such as aniline), an alkoxyarylamine, and an alkylarylamine.

It is noted that for an aminoaryl, for example, substituents that feature an inductive effect so as to enhance the electron donating property of the amine are beneficial, as discussed hereinabove. Thus, substituents such as aryloxy or alkyl, when positioned at the ortho or para position with respect to the amine are preferred.

It is to be further noted that stronger electron donating property of the functional moiety enables interaction with nitro-containing compounds which exhibit lower electron deficiency.

For example, while TNT exhibits a high extent of electron deficiency, compounds with less nitro substituents or aliphatic nitro-containing compounds can be less sensitive for a detection method that utilizes aminopropyl functional group, yet, such compounds will interact in a method that utilizes a stronger functional moiety such as, for example, N-methylpropylamine or 2-methoxyaniline.

In some embodiments, the functional moiety is covalently attached to the nanostructure's surface by means of covalent bonds formed between reactive groups within the functional moiety and compatible reactive groups on the surface of the nanostructures.

Reactive groups on the nanostructure's surface are either intrinsic or can be generated upon a suitable treatment. In some embodiments, where the nanostructure is SiNW or silicon nanotubes, free hydroxyl groups are intrinsically present on the surface of the nanostructures and can be utilized for attaching functional moieties thereto.

Alternatively, the nanostructures described herein are first surface-modified so as to generate surface reactive groups. Such a surface modification can be performed by, for example, attaching to intrinsic functional groups on the surface a bifunctional linker molecule, which comprises in one terminus thereof a reactive group that is capable of forming a bond with these intrinsic functional groups and in another terminus thereof a reactive group that can form a bond with the functional moiety.

In some embodiments, the functional moiety comprises, prior to being attached to the nanostructure, a reactive group that can readily react with a reactive group on the nanostructure surface so as to form a covalent bond with the surface.

Selecting reactive groups that are compatible with functional groups on the nanostructure of choice is within the capabilities of any person skilled in the art, particularly in view of the guidance provided herein.

In some embodiments, when the nanostructure is SiNW or silicon nanotubes, the functional moiety comprises a reactive group capable of forming covalent bond with free hydroxy groups on the nanostructure surface. Exemplary such reactive groups include, but are not limited to, halides and alkoxides, which can act as leaving groups so as to form an ether bond, carboxylic acids or esters, which can form an ester bond via esterification or trans esterfication, as well as halosilanes and orthosilicates, which can form —Si—O— bonds.

According to some embodiments of the invention, the functional moiety is attached to the nanostructure via any one of the bonds described herein.

In some embodiments, the functional moiety is an aminoalkyl and the aminoalkly is derived from an aminoalkyltriorthsilicate, such as, for example, aminopropyltriorthosilicate or N-methylaminopropylorthosilicate.

In some embodiments, the functional moiety is an aminoalkyl or an aminoaryl, and the aminoalkyl or aminoaryl is derived from aminoalkyl that is further substituted by halide or aminoaryl substituted by haloalkyl or aminoaryl substituted by triorthosilicate.

As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is a linking group.

Herein throughout, the phrase "end group" describes a group (a substituent) that is attached to another moiety in the compound via one atom thereof.

The phrase "linking group" describes a group (a substituent) that is attached to another moiety in the compound via two or more atoms thereof.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain.

The term "aminoalkyl" is used herein to describe an alkyl substituted by an amine, as defined herein. In some embodiments, the amine substitutes a terminal carbon atom in the alkyl.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

The term "amine-oxide" describes a —N(OR')(R") or a —N(OR')— group, where R' and R" are as defined herein. This term refers to a —N(OR')(R") group in cases where the amine-oxide is an end group, as this phrase is defined hereinabove, and to a —N(OR')— group in cases where the amine-oxime is an end group, as this phrase is defined hereinabove.

The term "halide" and "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$-linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "isocyanate" describes an —N=C=O group.

The term "nitro" describes an —NO$_2$ group.

The term "acyl halide" describes a —(C=O)R'" group wherein R'" is halide, as defined hereinabove.

The term "azo" or "diazo" describes an —N=NR' end group or an —N=N-linking group, as these phrases are defined hereinabove, with R' as defined hereinabove.

The term "C-carboxylate" describes a —C(=O)—OR' end group or a —C(=O)—O-linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

The term "C-thiocarboxylate" describes a —C(=S)—OR' end group or a —C(=S)—O-linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "C-amide" describes a —C(=O)—NR'R" end group or a —C(=O)—NR'-linking group, as these phrases are defined hereinabove, where R' and R" are as defined herein.

The term "N-amide" describes a R'C(=O)—NR"— end group or a R' C(=O)—N-linking group, as these phrases are defined hereinabove, where R' and R" are as defined herein.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R''' end group or a —R'NC(=N)— NR"— linking group, as these phrases are defined hereinabove, where R', R" and R''' are as defined herein.

The term "hydrazine" describes a —NR'—NR"R''' end group or a —NR'-NR"-linking group, as these phrases are defined hereinabove, with R', R", and R''' as defined herein.

The term "silyl" describes a —SiR'R"R''' end group or a —SiR'R"— linking group, as these phrases are defined hereinabove, whereby each of R', R" and R''' are as defined herein.

The term "siloxy" describes a —Si(OR')R"R''' end group or a —Si(OR')R"-linking group, as these phrases are defined hereinabove, whereby each of R', R" and R''' are as defined herein.

The term "silaza" describes a —Si(NR'R")R''' end group or a —Si(NR'R")— linking group, as these phrases are defined hereinabove, whereby each of R', R" and R''' is as defined herein.

The term "silicate" describes a —O—Si(OR')(OR")(OR''') end group or a —O—Si(OR')(OR")— linking group, as these phrases are defined hereinabove, with R', R" and R''' as defined herein.

As used herein, the term "hydrazide" describes a —C(=O)—NR'—NR"R''' end group or a —C(=O)—NR'—NR"— linking group, as these phrases are defined hereinabove, where R', R" and R''' are as defined herein.

As used herein, the term "thiohydrazide" describes a —C(=S)—NR'—NR"R''' end group or a —C(=S)—NR'—NR"— linking group, as these phrases are defined hereinabove, where R', R" and R''' are as defined herein.

As used herein, the term "methyleneamine" describes an —NR'—CH$_2$—CH=CR"R''' end group or a —NR'—CH$_2$—CH=CR"— linking group, as these phrases are defined hereinabove, where R', R" and R''' are as defined herein.

A Nanonose Device:

In some embodiments, the device comprises a plurality of nanostructures, which may, optionally and preferably, be arranged in addressable positions in which case the plurality of nanostructures is collectively referred to as a nanoarray (e.g., a nanowire array or a nanotube array). Also contemplated are embodiments in which the device comprises a bundle of randomly arranged nanostructures.

A nanoarray can comprise from dozens to thousands nanowires and/or nanotubes per square millimeter. The nanoarray can be fabricated using any technique known in the art, including, without limitation, the technique disclosed in U.S. Pat. No. 6,359,288, and U.S. Published Application Nos. 20050287788 and 200902561, the contents of which are hereby incorporated by reference.

The plurality of nanostructures in the array can be comprised of nanowires and/or nanotubes being modified in substantially the same manner, wherein each nanostructure is a modified nanostructure and all modified nanostructures have the same functional group attached thereto, thus enhancing the sensitivity of the device, due to the large number of functional moieties that can interact with the analyte.

In some embodiments, only a portion of the nanostructures includes modified nanostructures whereby the remaining nanostructures are unmodified.

Alternatively, at least a portion of the plurality of nanostructures comprises nanostructures having attached thereto a first functional moiety and at least another portion of the plurality of nanostructures comprises nanostructures having attached thereto a second functional moiety, the first and second functional moieties being different from one another. Such a device can comprise nanostructures having 2, 3, 4, 5, and even 10 or more differently-modified nanostructures, namely, nanostructures having different functional moieties attached thereto.

The different modifications can include, for example, functional groups with varying electron-donation properties, such that when a nitro-containing compound that has certain level electron deficiency contacts the device, its interaction with each of these functional groups results in a different change of the electrical property, and a response pattern that is indicative for each nitro-containing compound is obtained. The above is similarly effected for formulations containing a mixture of nitro-containing compounds.

Such a device for sensing nitro-containing compounds can act in analogy to an electronic olfactory receptor interchangeably referred to herein as "electronic nose" or "nanonose".

As known in the art, electronic nose devices perform odor detection through the use of an array of cross-reactive sensors in conjunction with pattern recognition algorithms. Each sensor in the electronic nose device is widely responsive to a variety of odorants, such that each analyte produces a distinct signature from the array of broadly cross-reactive sensors. Pattern recognition algorithms can then be applied to the entire set of signals, obtained simultaneously from all the sensors in the array, in order to glean information on the identity, properties and concentration of the vapors exposed to the sensor array.

In the context of embodiments of the present invention, a nanonose device, or an electronic nose device, acts by means of a plurality of nanostructures, e.g., a nano array, that contains several groups of nanowires and/or nanotubes, each group being modified with a different functional moiety. Each of the functional moieties in such a nanonose device has different chemical interactions with different nitro-containing compounds, and as a result, induces different changes in the electrical property of the respective nanostructure as a result of its interactions with different nitro-containing compounds.

These different changes translate into a response pattern obtainable by the device of the present embodiments, which response pattern being indicative of at least the type of nitro-containing compound or formulation contacting the nanonose device. Such a response pattern can be readily detected and processed.

A collection of nanostructures (e.g., an array) that functions as an electronic nose allows not only determining the amount and/or presence of a nitro-containing compound but also the identity, namely, the chemical composition, and thus can be used to differentiate between nitro-containing compounds and/or formulations.

A nanonose device suitable for the present embodiments can be fabricated in more than one way. In some embodiments of the present invention the nanostructures are first modified and thereafter deposited, for example, on a carrier substrate, to form the nanonose device. In these embodiments, different modifications of the nanostructures are optionally and preferably performed in different containers or vials from which the modified nanostructures are transferred to the carrier substrate, either as an array or as one or more randomly arranged nanostructure bundles. When the nanostructures form an array, at least two locations with different addresses, are preferably occupied by nanostructures with respective two different modifications.

In some embodiments of the present invention the nanostructures are first deposited on the carrier substrate, optionally and preferably in addressable locations (each location being associated with one or nanostructures), wherein the modification is performed in situ. In these embodiments the modifications are performed in accordance with the locations on the carrier substrate, such that for at least two locations with different addresses, a two different modification protocols are applied.

Figure 10A:
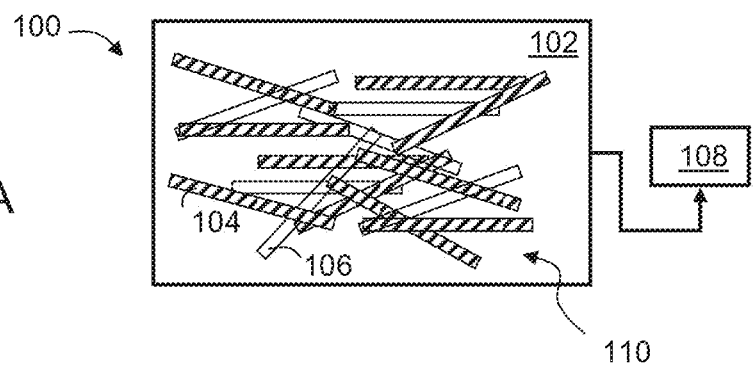
FIG. 10A illustrates a nanonose device in an embodiment of the invention in which the nanonose device comprises a plurality of randomly arranged nanostructures.
Figure 10B:
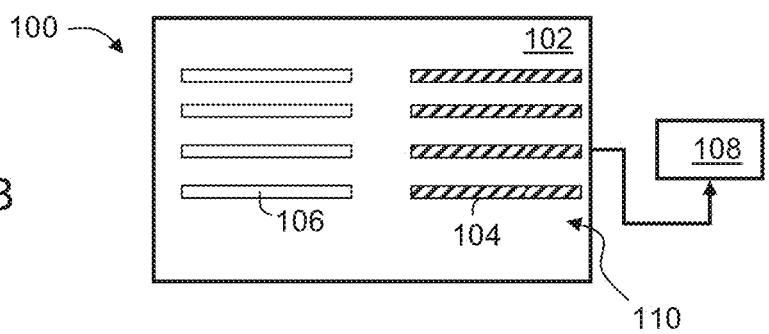
FIG. 10B illustrates a nanonose device in an embodiment of the invention in which nanonose device comprises a nanostructure array.

Representative examples of a nanonose device 100, according to some embodiments of the present invention are illustrated in FIGS. 10A and 10B, wherein FIG. 10A illustrates an embodiment in which nanonose device 100 comprises a plurality of randomly arranged nanostructures, and FIG. 10B illustrates an embodiment in which nanonose device 100 comprises a nanostructure array. Device 100 comprises a plurality of nanostructures generally shown at 110. nanostructures 110 comprises at least a first type of nanostructures 104 having attached thereto a first functional moiety (not shown) and a second type of nanostructures 106 having attached thereto a second functional moiety (not shown), the first and second functional moieties being different from one another. For clarity of presentation, nanostructures 104 are schematically illustrated as pattern-filled rectangles and nanostructures 106 are illustrated as non-filled rectangles. The nanostructures are deposited on a surface 102, preferably a solid surface, e.g., a surface of a substrate, such as, but not limited to, a silicon wafer. Nanonose device 100 further comprises a detector, symbolically illustrated at 108, for detecting the change in the electrical properties of the nanostructures. For example, nanostructures 110 can form a part of a transistor (e.g., a channel) as further detailed hereinabove, in which case the other parts of the transistor, as well as a suitable circuitry connected thereto form detector 108. Alternatively, a transistor is not employed, in which case detector 108 can be implemented as a measuring device for measuring the appropriate electrical property (e.g., resistance, conductance, capacitance, impedance, etc.) of the nanostructures.

When nanostructures 110 are arranged in addressable locations (FIG. 10B), detector 108 preferably receives signals separately from different locations. In these embodiments, detector 108 communicates with nanostructures 110 in a multiplexed manner, e.g., via a plurality of communication channels with minimal or no cross-talks thereamongst). When nanostructures 110 form a randomly arranged bundle (FIG. 10A), it is not necessary for detector 108 to communicate with nanostructures 110 in a multiplexed manner. It was found by the present inventors that in both configurations, a response pattern indicative of at least the type of the nitro-containing compound which contacts the nanonose device. The identification of the type of the nitro-containing compound for a given response pattern (e.g., an I-V curve), can be done, for example, using a look-up table or the like.

The Method:

The method is effected by contacting the device, as described herein, with the sample, as described herein.

By "contacting" it is meant bringing the sample and the device to a proximity that allows the detectable change in an electrical property of the nanostructure to take place. According to embodiments of the present invention, the detectable change results from an interaction between the functional moiety attached to the nanostructure and the nitro-containing compound. Thus, "a proximity that allows a detectable change" describes a proximity that allows the nitro-containing compound to interact with the functional moiety.

The term "contacting" encompasses "exposing".

In some embodiments, contacting the sample with a device can be performed by placing the device in an environment of the sample.

Thus, contacting the device with the sample can be effected by placing the device is a liquid sample, or by passing the liquid sample through or on the device. Alternatively, contacting the device with the sample can be effected by passing a stream of gaseous sample through or on the device, or, simply by placing the device in a proximity of a substance suspected as containing a nitro-containing substance.

The method is further effected by qualitatively or quantitatively determining a change in the electric property of the nanostructure.

The term "determining" thus refers to a quantitative or qualitative analysis via any electric measurement known in the art.

Once the device has been performed and an analyte is detected, regeneration of the device can be effected by washing the device, optionally using an aqueous solution containing an organic solvent.

In various exemplary embodiments of the invention several devices are distributed over a region-of-interest to allow detecting the presence and/or an amount of the nitro-containing compound in two or more locations over the region-of-interest. The region-of-interest can include any region in which it is desired to at least identify presence of nitro-containing compound, including, without limitation, large public places e.g., airport, mall, academic institute, restaurant, theater, vehicles, e.g., an airplane or a boat, and the like.

The devices can occupy static and locations over the region-of-interest, or in the alternative, they can be released to the region-of-interest by placing them on vectors in the environment.

As used herein, a "vector" refers to an entity having a self-relocating ability. For example, a "vector" can be a civilian, a law-enforcement officer, a vehicle, an animal and the like.

The devices can be connected over a communication network, for example, wireless local area network (WLAN), WiFi® network, Bluetooth® network, cellular network and the like. Preferably, the devices are connected to more than one communication network to allow operation also in regions not covered by a particular network.

When the devices are placed on vectors, they are optionally and preferably supplemented by positioning units to allow them to transmit location data over the network. Many positioning technologies are contemplated. Representative examples include, without limitation global positioning systems, commonly known as GPS, network based positioning, in which the location of the device is computed by triangulation of its signal between transmission towers, motion-based positioning in which the location is calculated based on the motion parameters of the device, and cell-identification in which the environment is divided into a plurality of geometric elements and each entry of the device into a respective element is monitored and recorded.

In various exemplary embodiments of the invention the devices are monitored at a central location. The monitoring can be done in terms of detection events as well as in terms of locations. The monitoring can be done either continuously, or at predetermined times as desired. The central location can use the information acquired from the devices to perform risk analysis and, based on the analysis, to notify the appropriate authorities (decontamination divisions, medical teams, low enforcement, mass communication channels, etc.) of the location of the detected compound.

Upon a detection event generated by a detector of particular device, other devices, identified as being nearby to the particular device, are signaled to carry out corresponding detection tests, to thereby confirm or localize the initial detection.

As will be appreciated by one ordinarily skilled in the art, the use of many portable devices which communicate over the network and interchange detection and, optionally, location data can be used to detect presence, level and location of the compound and to distribute the information, substantially in real-time, both to the appropriate authorities and optionally also among the population. The activation of the nearby devices can be done either by instructing the respective vectors which carry the nearby detectors to locally activate the devices, or by performing a remote activation at the central location. Additionally, certain vectors can be alerted of the threat and instructed to take the necessary precautions.

It is to be understood that the activation of the devices can be done, irrespectively whether or not a detection event has been received. According to various exemplary embodiments of the present invention, the devices (or at least a portion thereof) are distributed in the environment in an inactive mode. The appropriate authorities can then decide, e.g., based on intelligence or other sources of information, to selectively activate devices which are located in a particular part of the region-of-interest. This can be done, for example, by transmitting activating signals to devices associated with one or more base stations of the communication network which cover the region. This embodiment is particularly useful when the devices are integrated in their inactive mode within accessories such as cellular telephones carried by the population, whereby each accessory is frequently communicating its nearest cellular base stations, and all the accessories which are associated with the same cellular base station define a region. Activating signals, transmitted through a particular cellular base station, activate only the devices of the defined region while keeping devices located in other regions in their inactive mode. It will be appreciated that this can prevent accidental activation and panic in all regions other than the region of interest.

The detection events can be clustered, by combining detection and location information received, e.g., at the central location. The clustering can serve both as confirmation for the presence, level and location of the compound, and also to define a diffusing signal, representing propagation of the compound. This can be achieved, for example, by repeating the clustering identification at different instants of time.

Figure 1C:
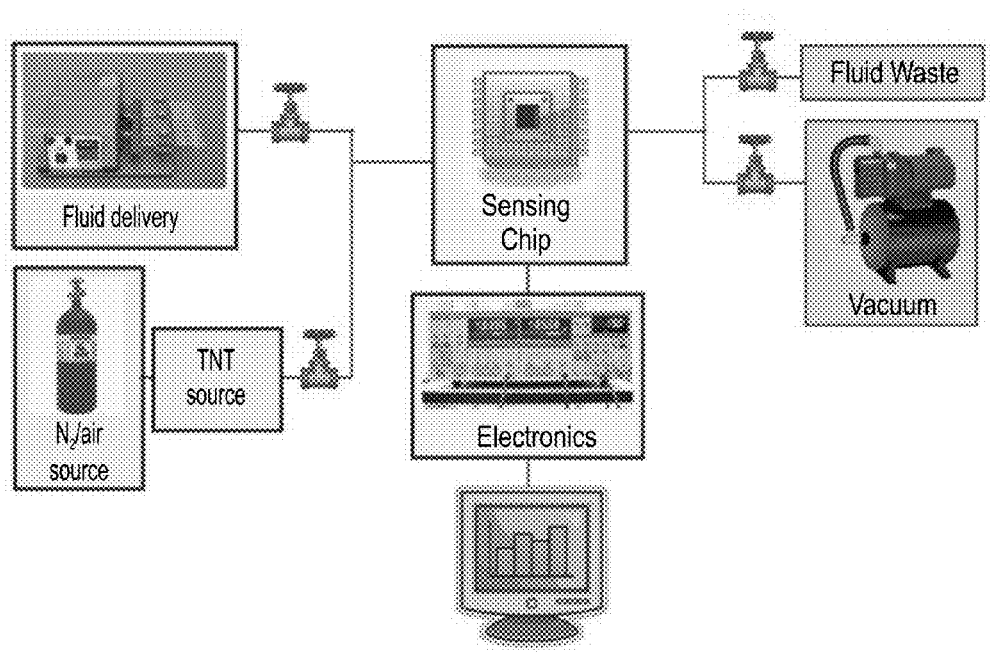

The Systems:

FIG. 11A is a schematic illustration of a system 120 for determining a presence and/or an amount of a nitro-containing compound according to some embodiments of the present invention. System 120 comprises a sensing device 122 and a processing unit 124. Device 122 preferably comprises one or more modified nanostructures and a detector as further detailed hereinabove. For example, device 122 can include a nanonose device, such as nanonose device 100, a transistor, such as transistor 20 or 50, or the like. In any event, device 122 produces a detectable signal indicative of presence or amount of the nitro-containing compound contacting the device. Processing unit 124, receives the signal from device 122 and processes it to at least determine the presence of a nitro-containing compound. Optionally and preferably processing unit 124 also determines at least one of the type and amount of the nitro-containing compound based on the response pattern it receives from device 122. System 120 can be configured such that device 122 is located at a position where the presence of nitro-containing compounds is suspected, and produces detection signals that are processed by unit 124. Unit 124 can be located next to device 122 or at a different (e.g., remote) location. The device and/or CPU can be static, mobile or portable. An exemplary prototype system is shown in FIG. 1C and described in the Examples section that follows.

Reference is now made to FIG. 11B, which is a schematic illustration of a distributed detection system 200, which can be used for determining a presence and/or an amount of a nitro-containing compound in a region-of-interest according to some embodiments of the present invention. System 200 can employ a plurality of sensing devices 202 which are deployed over the region-of-interest and configured for producing detection signals in the presence of the nitro-containing compound. The principles and operations of at least some of devices 202 are preferably the same as those of device 122 or system 120 described above. Devices can be deployed in static locations over the region-of-interest or they can be placed on vectors as further detailed hereinabove. System 200 further comprises a central processing unit 204 which communicates with devices 202 over a communication network as further detailed hereinabove. Devices 202 can also intercommunicate thereamongst, if desired, for example, to alert neighboring vectors in case of a detection event. Central monitoring unit 204 is preferably located at the aforementioned central location and performs various tasks therefrom. For example, unit 204 can remotely activate one or more of devices 202, monitor detection and location data transmitted by devices 202, cross check detection information of several devices, identify clustering, providing indication pertaining to propagation of the nitro-containing compound, and communicate with the vectors carrying the detectors, as further detailed hereinabove.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Nanowire FET Fabrication

Silicon nanowires (SiNWs) were synthesized by chemical vapor deposition (CVD) with the use of 20 nm gold nanoparticles as catalysts and silane as reactant. Diborane was used during the growth to provide boron as a p-type dopant with a B:Si ratio of 1:4000. The FETs were fabricated by photolithography. Briefly, passivated source and drain electrodes were deposited with the use of a multilayer photoresist structure consisting of 300 nm LOR3A (Microchem) and 500 nm 1805 (Shipley). After exposure and development of the electrode pattern, the contacts were metallized by e-beam and thermal evaporation of Ti/Pd (5/60 nm) respectively and were then passivated from the electrolyte with an insulating layer of $Si_3N_4$ (50 nm-thick) deposited by plasma-enhanced chemical vapor deposition (PECVD). The separation between the source and drain electrodes for each FET was 2 µm. Last, the chip was coated with a 100 µm SU-8 3050 photoresist (Microchem Inc.) and a channel was defined over the NW device regions by photolithography.

Example 2

Fluid-Delivery System

The fluid-delivery device was fabricated from flexible polydimethylsiloxane (PDMS) elastomer mixed in a 10:1 ratio of base to curing agent. The PDMS was cured overnight in an oven at 60° C. and then cut into rectangular pieces. The dimensions of the PDMS were 10×10×5 mm (length×width×height). The lithographically-defined SU-8 channel sealed by the PDMS elastomer created a fluid delivery system.

Example 3

Surface Modification of Nanowire Device

The chemical modification of the sensing elements and the electrical-transport characteristics of the devices obtained were studied. Amino-functionalized layers were prepared by self-assembling 3-aminopropyltriethoxysilane (APTES) on silicon-nanowire devices in aqueous solutions for varied deposition times.

The sensor device was cleaned with oxygen plasma, so as to obtain clean and oxidized nanowire-device surfaces for the effective chemical modification with 3-aminopropyltriethoxysilane to provide amino groups at the nanowire surface. The chip was first treated with 1% (v/v) 3-aminopropylethoxysilane (APTES) (Aldrich) in 95% ethanol, and was allowed to stand for 20 minutes before filtering through a 0.2 µm-cutoff syringe filter. The plasma-cleaned sensor chip was immersed in the silane/ethanol solution for 30 minutes and then the chip was rinsed with ethanol, dried in a stream of nitrogen gas and baked at 150° C. for 5 minutes.

Additional aminosilane derivatives, such as N-methyl aminopropyltriethoxysilane, were used for modifying nanowire-device surface similarly to APTES. Similarly, for comparison, surfaces were modified by octadecyldimethylchlorosilane and fluorosilane derivatives using a 2% solution of the silane derivative in ethanol and dichloromethane, respectively.

Ellipsometry measurements were performed in all samples for proper characterization of molecular layer thickness.

Fourier transform infrared spectroscopy (FTIR) and ellipsometry have shown that the structure and thickness of APTES films are governed by the deposition time and reaction solution [Howarter, J. A. & Youngblood, Langmuir 22, 11142-11147 (2006)]. APTES films of thickness ranging from 6.5 to 12 Å (between a monolayer and a bilayer) are generally formed when deposition is conducted in aqueous solutions.

XPS Analysis

X-ray Photoelectron Spectroscopy (XPS) measurements were performed in UHV ($2.5 \times 10^{-10}$ Torr base pressure) using 5600 Multi-Technique System (PHI, USA). The samples were irradiated with an Al $K_\alpha$ monochromated source (1486.6 eV) and the outcome electrons were analyzed by a Spherical Capacitor Analyzer using the slit aperture of 0.8 mm C1s at 285 eV was taken as an energy reference. The samples were analyzed on the surface only.

The following measurements were performed:

Survey: spectrum in a wide energy range (0-1400 eV), which gives an estimation of the elements present on the sample surface and is taken at a low resolution.

Utility Multiplex: spectra taken for different peaks in a low energy range window at an Intermediate (Utility) Resolution.

It is taken for all the elements present for the atomic concentration (AC %) calculation. An AC table is given as an output of these measurements. AC calculation accuracy:

±2% for AC around 50%
±5%-20%
±10%-5%
±20%-1%

High Resolution Multiplex: spectra taken for different peaks in a low energy range window at a High Resolution (PE=11.75 eV, 0.05 eV/step). These measurements allow precise energy position and peak shape determination, necessary for bond bonding analysis.

The following samples were characterized:
1. Silicon/SiO sample without modification as reference.
2. Silicon/SiO sample modified with APTES for 10 minutes after filtering of solution.
3. Silicon/SiO sample modified with APTES for 20 minutes after filtering of solution.
4. Silicon/SiO sample modified with APTES for 20 minutes without filtering of solution.

The XPS measurements confirm the formation of an APTES layer as expected, and further validate the presence of surface modified amino and ammonium groups (data not shown).

Performance Measurements

The dependence of the source-drain current (ISD) on source-drain voltage (VSD) for varying gate-drain voltages (VGD) for a representative device, before any chemical modification is performed, is shown in FIG. 1D. As shown in FIGS. 1E and 1F, surface functionalization with 3-aminopropyltriethoxysilane to convert silanol (Si—OH) groups to free amines has no deleterious effect on the electrical properties of the device.

Example 4

Liquid-Phase Detection of TNT

To assess the efficacy of the herein described system for the sensing of TNT, aqueous solutions (DI water containing 0.1% DMSO) spiked with TNT at concentrations ranging from 500 fM to 5 µM were delivered to the sensor chip device through a built-in-chip fluid delivery system (see, FIG. 1C).

TNT, prepared according to Dorey and Carper [Journal of Chemical and Engineering Data 29, 93-97 (1984)], was dissolved in 0.1% DMSO in a DI $H_2O$ and was delivered to the chip by the microfluidic system by means of a syringe pump (Dolomite Mitos Syringe Pump XS) at a flow rate of 5 µl/minute (The action of injecting the solution might introduce some negligible noise into the electrical read-out signal). All studies were carried out at room temperature.

The conductance of the silicon nanowire FET was measured by application of AC bias (70 kHz, 30 mV) by means of a lock-in amplifier (Stanford Research System model SR830 DSP). The drain current was amplified with a variable-gain amplifier (model 99539 Amplifier System) and filtered by the lock-in amplifier with a time-constant setting of 300 ms. The output data were recorded by using a multichannel I/O adaptor panel (BNC-2090, National Instrument).

Figure 2A:
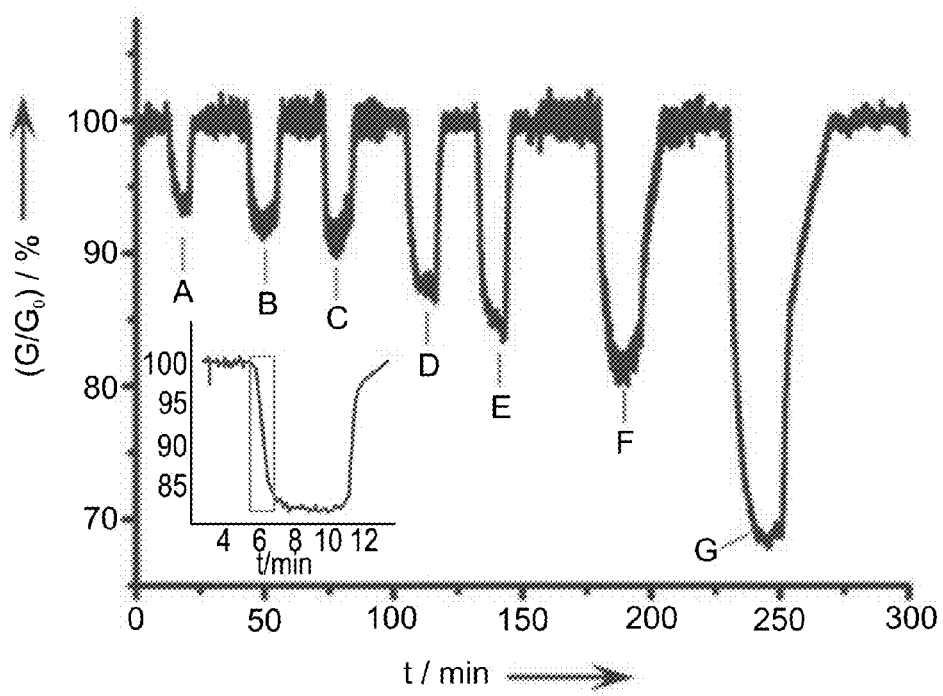
Figure 2B:
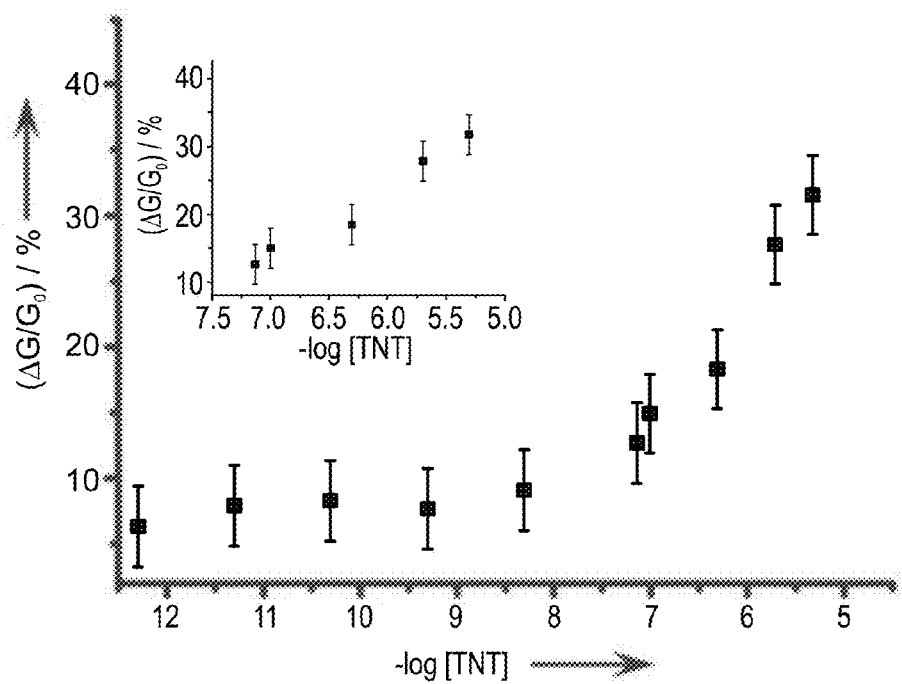
Figure 2C:
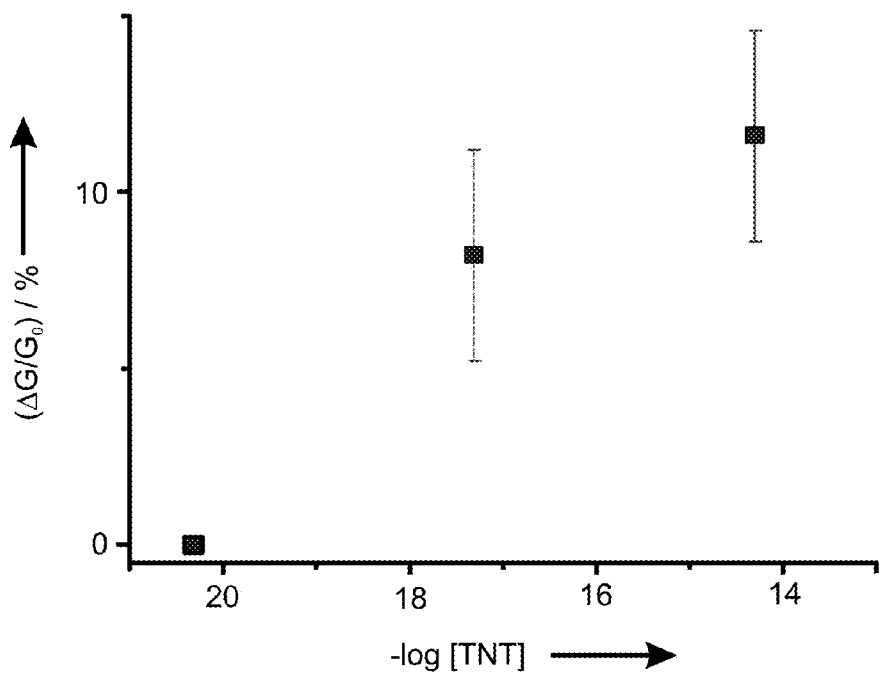

The obtained data are presented in FIGS. 2A and 2B, and show that the conductance of the nanowires is extremely sensitive to the presence of TNT over the whole concentration range, and displays a well-defined increase and subsequent return to baseline when TNT solution and reference washing solution (DI water containing 0.1% DMSO), respectively, are alternately delivered through the fluid delivery system to the devices. A plot of these data shows (FIG. 2B) that the change in conductance is directly proportional to the TNT concentration for values from 50 µM down to 5 nM. The nanosensors can unmistakably detect TNT down to concentrations well below the femtomolar level (about 0.5 femtomolar). Even further, the most sensitive devices can sense TNT down to the 50-100 attomolar range (see, FIG. 2C). It is to be noted that the nanosensors described herein are composed of an array of modified nanowires, each functioning as a sensor device. In addition, sensing can be performed rapidly—in less than a minute—without the need for pre-concentration steps.

Generally, the binding of electron-deficient TNT to the amino groups on the nanosensor surface is expected to lead to the formation of charge-transfer complexes [Xie et al., *Anal. Chem.* 2008, 80, 437; Sharma, *Spectrochimica Acta Part a—Molecular and Biomolecular Spectroscopy* 2008, 70, 144], which act as effective molecular gating elements and strongly modulate the electrical conductance of the nanosensing elements. For example, 2,4,6-trinitrotoluene (TNT) is almost less in solution and does not absorb any visible light. Previous investigations have demonstrated that a solution of TNT changes from colorless to deep red after the addition of organic amines such as 3-aminopropyltriethoxysilane (APTES) [see, e.g., Gao et al., *Anal. Chem.* 2008, 80, 8545]. Two kinds of strong interactions may occur between the electron-deficient aromatic ring of TNT and the electron-rich amino group of APTES. The charge transfer from amino groups to aromatic rings leads to the formation of Meisenheimer complexes between TNT and primary amine groups. Meanwhile, as a commonly accepted mechanism, a TNT molecule is a Bronsted-Lowry acid and can be deprontonated at the methyl group by a basic amine. The negative charge on the TNT anion is distributed throughout the molecule through resonance stabilization by three electron-withdrawing nitro groups, leading to the formation of the acid-base pairing interaction. The TNT anions or TNT-amine complexes can strongly absorb the green part of visible light, and therefore the color of solution changes into deep red. By both mechanisms, the reversible complexation of uncharged TNT molecules with surface amino groups leads to the formation of charges in close proximity to the sensing surface, thus, leading to abrupt changes in the devices conductance.

Without being bound by any particular theory, the following is noted in view of the surprising data obtained in these studies:

(1) The charges on dissolved molecules and macromolecules are screened by dissolved counter-ions. As a result of the screening, the electrostatic potential arising from charges on the analyte molecule decays exponentially toward zero with distance [Stern et al., Nano Letters 7, 3405-3409 (2007)]. Thus, for optimal sensing, the Debye length is preferably carefully selected for nanowire-FET measurements. In previously reported cases, molecules bound to the devices are separated from the sensor surface by about 2-12 nm (the size of the receptor proteins or DNA linkers bound to the sensor surface). By contrast to those cases, the APTES recognition elements in the exemplary devices described herein are short organic molecules, about 0.6 nm in length (see, FIG. 1A), the amino groups of which are in close proximity to the surface of the nanowire sensing elements.

(2) The fact that the recognition elements are not of a biological nature enables the use of a virtually salt-free solution (i.e. DI water). The Debye length, $\lambda$, is expected in this case to be around 1 μm. This large screening length results in extremely high sensitivities in the sensing of the charge-transfer-complex pairs formed between TNT molecules and the amino groups on the nanowire surface.

Figure 2D:
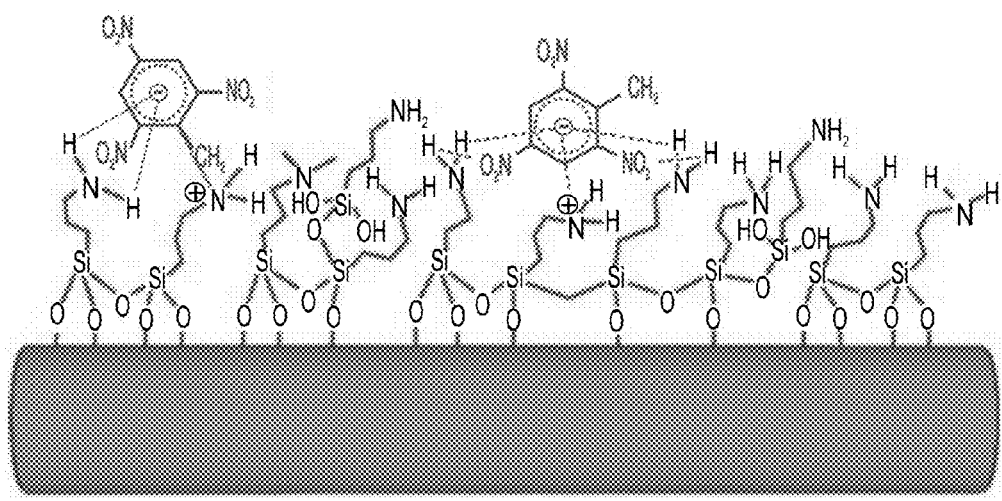

(3) The formation of the charge transfer complex between a TNT molecule and an amino functional group on the nanowire can be further stabilized by the presence of neighboring amino groups on the surrounding surface area. The negative charge formed on the surface-complexed TNT molecule can be further accommodated and stabilized by neighboring ammonium groups on the surface, thus leading to more stable charge transfer complexes and enhanced sensitivities as experimentally observed (see, FIG. 2D).

Electrical Transport characteristics

The chemical modification of the sensing elements and the electrical-transport characteristics of the devices obtained were first studied. Ellipsometry results have shown that the thickness of the APTES layer obtained generally ranges from 6.5 to 12 Å (between a monolayer and a bilayer) and that the structure and thickness of APTES films are governed by the deposition time and the composition of the silane solution as expected [J. A. Howarter, J. P. Youngblood, *Langmuir* 2006, 22, 11142].

Reversibility, Cross-Reactivity and Stability

In a real-time field sensor, the reversibility (the ability of the sensor to return to its initial state) and the response time of the sensor should be considered. As seen in FIG. 2A inset, the change in conductance begins immediately upon exposure of the nanowire device to the TNT solution, and stabilizes at a new value over a period of a few minutes. This holds even for the highly diluted 500 fM TNT solution. In addition, when the reference washing solution containing no TNT is introduced into the system, after TNT had been flowing through the sensors, the device again responds very rapidly, and the conductance returns to its baseline value.

Figure 3:
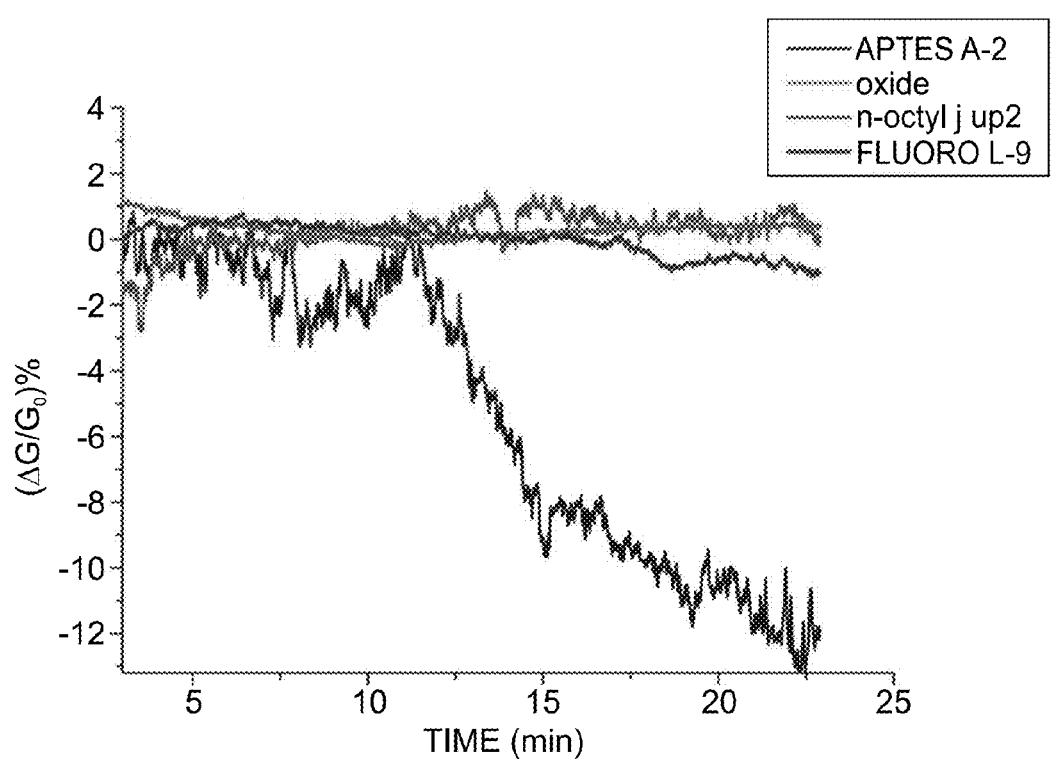

Control 'unmodified' nanowire devices on the same chip, as well as devices modified with alkyl- and fluoroalkyl-silane derivatives did not yield any observable signal upon interaction with high concentrations of TNT, 5 μm, or other nitroaromatic species (see FIG. 3). This fact indicates that TNT indeed forms complexes with surface amino groups as stated before.

Figure 4:
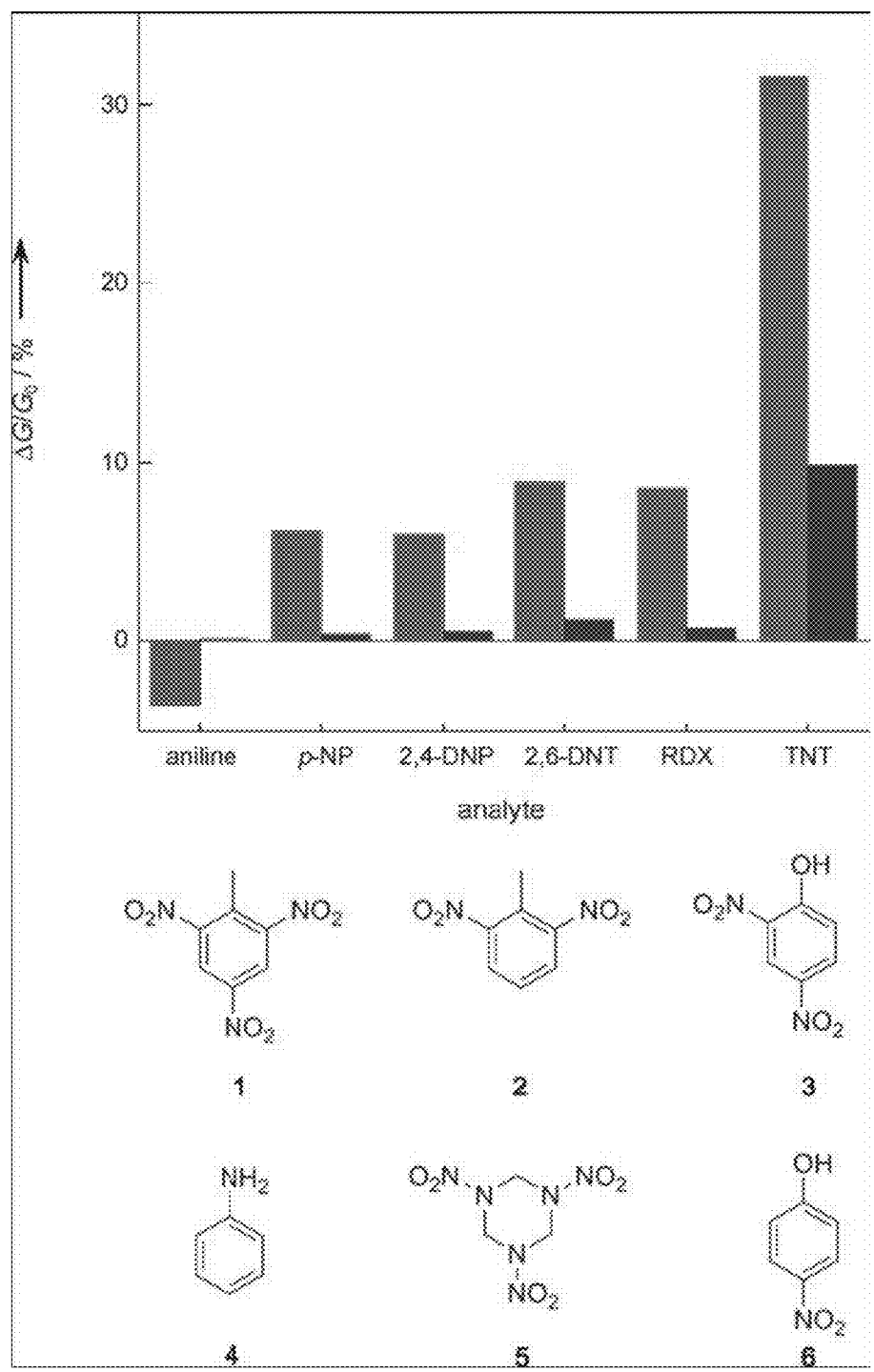

Cross-reactivity of the sensor to structurally related nitroaromatic chemical derivatives was also investigated (see, FIG. 4). The results clearly show a preference for binding TNT over these compounds. Analysis of these results reveals that molecules with a higher ability to create charge-transfer complexes with the amino-modified monolayer, such as TNT and 2,4-dinitrotoluene (2,4-DNT, Compound 2), induce a stronger conductivity change than other nitro-aromatics of a less electron-withdrawing nature. The latter materials cause changes in the conductance of the device only at concentrations greater than 5 μM, orders of magnitude higher than that for TNT. Aniline (Compound 4) does not cause any decrease in conductivity, but a slight increase only at very high concentrations (>50 μM), suggesting the formation of surface dipoles of opposite sign caused by the interaction of this molecule with the surface APTES layer. At concentrations lower than 5 nM, interferent materials do not give rise to appreciable signals. These data provide support for the proposed charge-transfer interaction of TNT with the APTES-modified SiNW device.

In addition, solutions containing common nitroaromatic compounds believed to be interferents in the detection of TNT (see, Compounds 7-9, FIG. 4), and currently widely used as additives in fragrances and other cosmetics, do not lead to any detectable signals at the concentration levels studies. These materials, as a result of the presence of multiple electron-donating groups on the aromatic ring and their lower number of nitro groups, are less effective, or incapable, of forming charge-transfer complexes at the concentration range under investigation.

In order to improve the detection limit of a sensor, it is advisable to have high gain yet also to reduce the noise level, and to provide a high signal-to-noise ratio, thus also preventing the large number of false positives and false-negatives, intrinsic to current-sensing technologies. One strategy to achieve this goal is to employ a large number of identical sensors simultaneously for the same analyte molecule to enhance the signal-to-noise ratio.

Figure 5A:
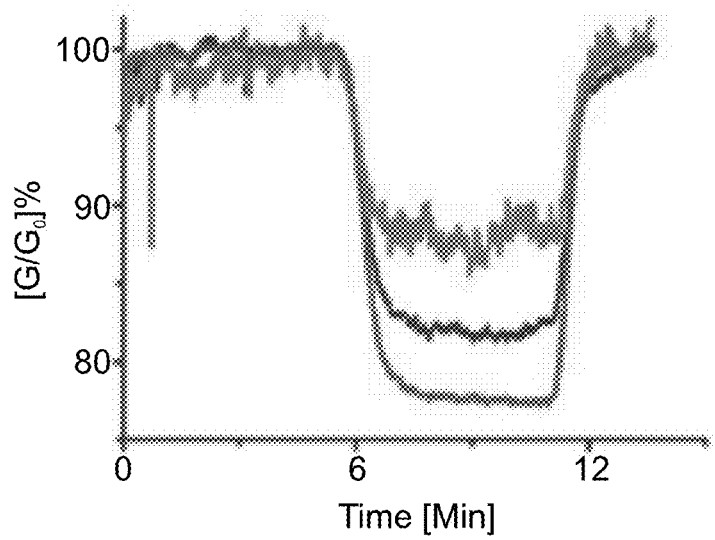
Figure 5B:
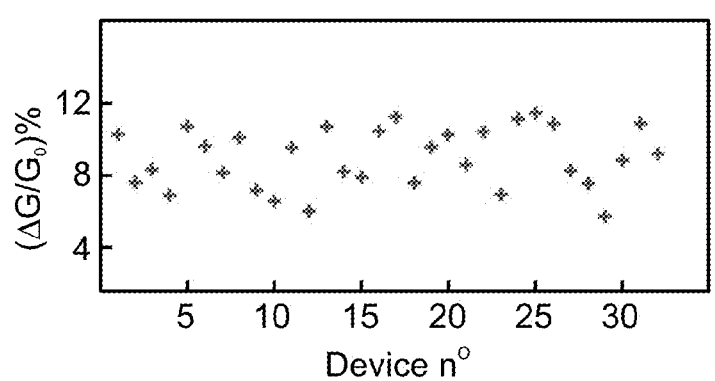

The sensor chip described herein is designed to contain close to 200 devices that could potentially perform the simultaneous detection of TNT. To demonstrate this, the detection of TNT simultaneously by three nanowire-devices was performed. As shown in FIG. 5A, all devices behave almost identically, showing the expected decrease in conductance upon exposure to TNT and subsequent increase when the latter is washed away. As shown in FIG. 5B, the same was observed for most of the working devices in a single chip. Thus, reliable ultra-trace sensing arrays, which can readily detect ultra-low concentrations of explosive molecules, with a detection limit lower than the vapor pressure of most explosives at room temperature, are demonstrated herein. This allows for the sensing of most species, directly from air-collected samples without the need for pre-concentration.

Figure 5C:
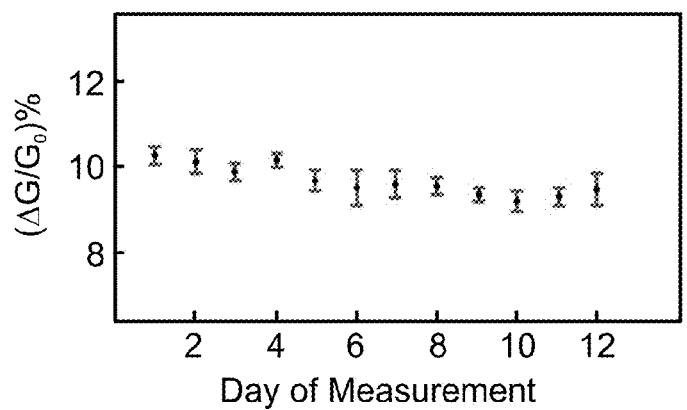

Another observation is that about 100 repeated TNT injection/wash cycles with the same nanowire device were performed for over more than a week, and found remarkable sensing stability and reproducibility (see, FIG. 5C).

Example 6

Gas Phase TNT Detection

The nanowires FET arrays described herein were tested for their capability to sense TNT directly from air samples. TNT is able to form Meisenheimer complexes and acid-base pair complexes with amino groups even in the gas phase [Jehuda et al., *J. Mass Spect.* 2005, 30, 715]. The gas-phase detection of TNT vapor was conducted with the same detection set-up, but using either a nitrogen-gas or dry-air stream as the carrier of TNT vapor to the sensing chip. Delivery lines were heated to 80-90° C., in order to prevent condensation of TNT vapor and adsorption to the plastic lines. The TNT source, through which nitrogen or dry air was passed, was kept at room temperature (25° C.).

The TNT vapor was generated by passing nitrogen gas through a vial containing tiny amounts of TNT (<100 μgr), with inlet and outlet gas ports. The TNT source is heated on a heating element at 60-90° C. The TNT vapor generated is delivered through PEEK and polyethylene tubes ($\frac{1}{16}$ inch inner diameter). Thus, the TNT vapor was delivered into the sensing chip by passing nitrogen gas (or compressed dry air) through a stainless steel vial containing small amounts of TNT (100 g-2 mg), with inlet and outlet gas ports. The TNT source vial temperature can be controlled between 5-150° C., in order to control the equilibrium vapor pressure of the TNT material (or any other explosive molecule). The flow of nitrogen carrier or compressed dry air is controlled by the use of MKS mass flow controllers (from 0.1 to 200 ml·min$^{-1}$).

Initially, the carrier gas (dry $N_2$ or dry compressed air) is passed through the reference tube directly into the device. After a stable electrical signal has been obtained, the flow is diverted to the TNT source by short time pulses of 2-5 seconds. When there is no TNT in the vial, no change in the signal is observed. Regeneration of the device is accomplished by simply washing the sensor chip with 0.1% DMSO in DI $H_2O$.

A MFC-controlled gas carrier line flows through the explosive-containing temperature-controlled vial after reaching its equilibrium vapor pressure at a given temperature (about 7 ppb at 25° C. for TNT). If required for concentration-dependence sensing of TNT, the explosive vapors can be readily diluted using a series of MFC-controlled diluting gas lines, mixing their flowing gas with the TNT-vapor gas line before reaching the sensing set-up, always keeping the total flow constant by the use of a MFC (1-5 sccm). All gas lines leading to the sensing chip are heated to 120° C. to prevent condensation of explosive vapors on the delivery lines and thus, large deviations of explosives effective concentrations. Absence of TNT in the vial leads to no change in the signal of sensing devices. Regeneration of the devices is accomplished by simply washing the sensor chip with 0.1% DMSO in DI $H_2O$. In order to prevent potential humidity interferences, the carrier gases can be loaded with a controlled humidity extent (35-60%) or dried using a drying pre-column Regardless, in the gas/vapor sensing experiments described herein, the electrical sensing nanowire array 'baseline' signal is first stabilized with the gas carriers in the absence of TNT, followed by short pulses of TNT-containing vapors, thus no effect of humidity is observed.

Figure 6:
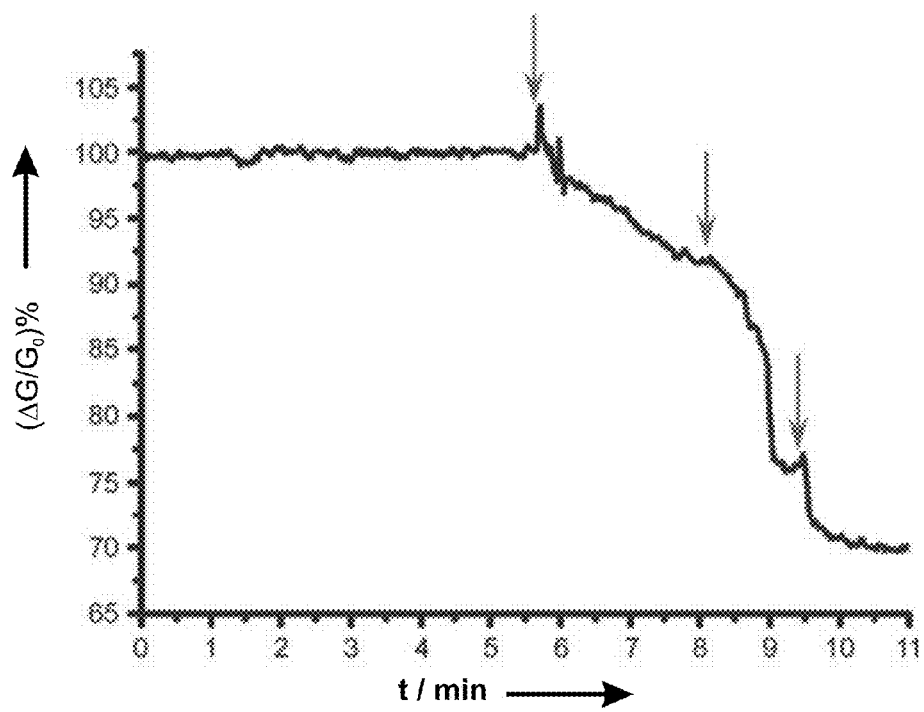

As shown in FIG. 6, the presence of TNT vapor is easily and rapidly detected by the nanosensor array. It is noted that the vapor pressure of TNT at 20° C. is about 10 ng/l or 1 ppb. The TNT-delivery line is open to the detection system for only two seconds before it is closed again, thus exposing the sensing array to very short pulses of TNT-containing vapor of controlled concentration. This shows that the nanosensors are extremely sensitive to the presence of TNT in air and that long sampling and most importantly, that pre-concentration steps, are not required. The sensing of TNT in air could be performed for tens of cycles at low concentrations of TNT (between ppb and ppt concentrations), with a sensitivity limit similar to that measured in solution sensing experiments. If required, the sensor surface can be readily reactivated by a short washing step in water/0.1% DMSO solutions. This removes any TNT molecules bound to the sensing surface through charge-transfer complexes, and brings it back to its initial baseline state. Additionally, no influence of humidity and odor materials was detected at the tested experimental conditions.

The sensing of TNT vapors directly and rapidly from air-collected samples without pre-concentration, and the effective complete regeneration of sensing elements, suggest a role of the arrays described herein in detection of explosives and other chemical substances. The sensors used for TNT-vapor detection in air samples exhibit exceptional reliability and stability over periods of weeks without significant degradation of performance.

Figure 7A:
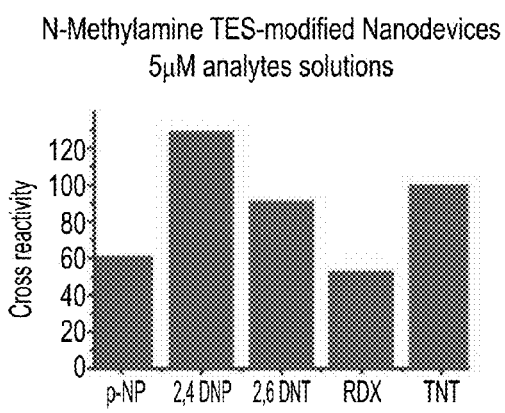
Figure 7B:
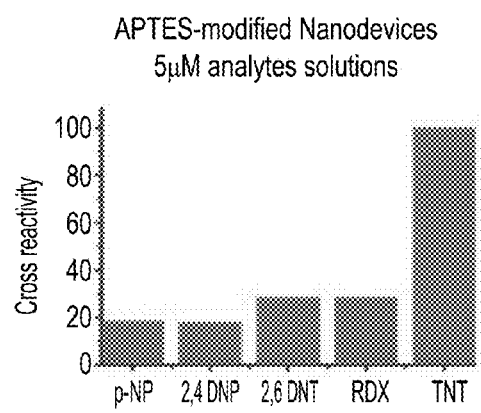

Additionally, no influence of humidity and odor materials (Compounds 7-9) was detected at the above-indicated experimental conditions (see, FIG. 7).

Example 7

Stimulation of Olfactory Sensing System

Additional experiments were focused on the modification of subgroups of nanosensors in a single array with a broad number of amine derivatives, each having different electron-donating capabilities, thus simulating a simple olfactory sensing system.

The results are presented in FIG. 7. Devices colored blue were modified with a stronger electron-donating amine derivative N-methylaminopropyltriethoxy silane. Devices colored in red were modified with APTES. Bars values are an average of the signal obtained by 20 devices modified with APTES and 20 devices modified with N-methylamineTES, respectively. STD values are about 10% of reported values. Clearly, using different amine derivatives of different electron-donating characteristics render the sensing and simultaneously identifying different explosive species, simulating a simple olfactory system.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of determining a presence and/or an amount of a nitro-containing compound in a sample, the method comprising contacting the sample with a device comprising a semiconductor nanostructure and a functional moiety attached to said nanostructure, wherein said functional moiety has a length smaller than 2 nm, is an electron-donating moiety, and interacts with the nitro-containing compound by forming a charge transfer complex and, and wherein said nanostructure is selected from a nanowire and a nanotube, and is disposed between a source electrode and a drain electrode, said nanostructure being such that upon contacting a sample that contains the nitro-containing compound, a detectable change in an electrical property of the nanostructure is exhibited, said change being indicative of the presence and/or amount of the nitro-containing compound in the sample.

2. The method of claim 1, wherein the sample is a fluid sample.

3. The method of claim 1, wherein the sample is air.

4. The method of claim 1, wherein a concentration of the nitro-containing compound in the sample is lower than 1 micromolar.

5. The method of claim 1, wherein said functional moiety is selected from the group consisting of $C_{1-10}$ alkyl, $C_{1-10}$ alkenyl, aryl and cycloalkyl, each being substituted by an electron donating group.

6. The method of claim 1, wherein said functional moiety is an aminoalkyl, said alkyl being 1-10 carbon atoms in length.

7. The method of claim 1, wherein said functional moiety is selected from the group consisting aminopropyl and N-methylaminopropyl.

8. The method of claim 1, wherein said device further comprises a detector constructed and arranged to determine a change in a source-drain current flowing through said nanostructure and resulting from said change in said electrical property of the nanostructure.

9. The method of claim 1, wherein said device further comprises a substrate onto which said nanostructure is deposited.

10. The method of claim 9, wherein said device comprises a plurality of said nanostructures being deposited onto said substrate, each of said nanostructures being independently selected from a nanowire and a nanotube and is being disposed between said source electrode and said drain electrode.

11. The method of claim 10, wherein said nanostructures are either substantially identical or at least a portion of said plurality of nanostructures comprises nanostructures having attached thereto a first functional moiety and at least another portion of said plurality of nanostructures comprises nanostructures having attached thereto a second functional moiety, said first and second functional moieties being different.

12. An electronic nanonose comprising a substrate and a plurality of nanostructures deposited onto said substrate, at least a portion of said plurality of nanostructures comprises nanostructures having attached thereto a first functional moiety and at least another portion of said plurality of nanostructures comprises nanostructures having attached thereto a second functional moiety, wherein said first and second functional moieties are different and each independently has a length smaller than 2 nm, is an electron-donating moiety, and interacts with a nitro-containing compound by forming a charge transfer complex, and wherein each of said nanostructures is independently selected from a nanowire and a nanotube, and is disposed between a source electrode and a drain electrode, said plurality of nanostructures being such that upon contacting a sample that contains said nitro-containing compound, a detectable change in an electrical property of said plurality of nanostructures is exhibited, said change being indicative of the presence and/or amount of said nitro-containing compound in said sample, and is further being indicative of the chemical composition of said nitro-containing compound.

13. The electronic nanonose of claim 12, wherein at least one of said first functional moiety and said second functional moiety is selected from the group consisting of $C_{1-10}$ alkyl, $C_{1-10}$ alkenyl, aryl and cycloalkyl, each being substituted by an electron donating group.

14. The electronic nanonose of claim 12, wherein at least one of said first functional moiety and said second functional moiety is an aminoalkyl, said alkyl being 1-10 carbon atoms in length.

15. The electronic nanonose of claim 12, wherein at least one of said first functional moiety and said second functional moiety is selected from the group consisting aminopropyl and N-methylaminopropyl.

16. The electronic nanonose of claim 12, further comprising a detector constructed and arranged to determine a change in a source-drain current flowing through said nanostructures and resulting from said change in an electrical property.

17. A system comprising a device which comprises a semiconductor nanostructure and a functional moiety attached to said nanostructure, wherein said functional moiety has a length smaller than 2 nm, is an electron-donating moiety, and interacts with a nitro-containing compound by forming a charge transfer complex, and wherein said nanostructure is selected from a nanowire and a nanotube, and is disposed between a source electrode and a drain electrode, said nanostructure being such that upon contacting a sample that contains said nitro-containing compound a detectable change in an electrical property of said nanostructure is exhibited, said change being indicative of the presence and/or amount of the nitro-containing compound in the sample, said device being in communication with a central processing unit, the system being for providing indication of a presence and/or amount of said nitro-containing compound in an environment of said device.

18. The system of claim 17, wherein said functional moiety is selected from the group consisting of $C_{1-10}$ alkyl, $C_{1-10}$ alkenyl, aryl and cycloalkyl, each being substituted by an electron donating group.

19. The system of claim 17, wherein said functional moiety is an aminoalkyl, said alkyl being 1-10 carbon atoms in length.

20. The system of claim 17, wherein said functional moiety is selected from the group consisting aminopropyl and N-methylaminopropyl.

21. The system of claim 17, wherein said device further comprises a detector constructed and arranged to determine a change in a source-drain current flowing through said nanostructure and resulting from said change in electrical property.

22. The system of claim 17, wherein said device comprises or is part of a transistor.

23. The system of claim 17, wherein said device further comprises a substrate onto which said nanostructure is deposited.

24. The system of claim 23, wherein said device comprises a plurality of said nanostructures being deposited onto said substrate, each of said nanostructures being independently selected from a nanowire and a nanotube and is being disposed between said source electrode and said drain electrode.

25. The system of claim 24, wherein said nanostructures are either substantially identical or at least a portion of said plurality of nanostructures comprises nanostructures having attached thereto a first functional moiety and at least another portion of said plurality of nanostructures comprises nanostructures having attached thereto a second functional moiety, said first and second functional moieties being different.

26. A distributed detection system comprising:
a plurality of sensing devices, each of said devices independently comprising a semiconductor nanostructure and a functional moiety attached to said nanostructure, wherein said functional moiety has a length smaller than 2 nm, is an electron-donating moiety, and interacts with a nitro-containing compound by forming a charge transfer complex, and wherein said nanostructure is selected from a nanowire and a nanotube, and is disposed between a source electrode and a drain electrode,
said nanostructure being such that upon contacting a sample that contains said nitro-containing compound a detectable change in an electrical property of the nanostructure is exhibited, said change being indicative of the presence and/or amount of the nitro-containing compound in the sample,
said plurality of sensing devices being deployed over an area and configured for producing detection signals in the presence of said nitro-containing compound; and
a central processing unit, communicating with each of said sensing devices and configured for processing said signals and providing indication of presence, amount, location and/or distribution of said nitro-containing compound in said area.

\* \* \* \* \*